United States Patent
Lee et al.

(10) Patent No.: US 12,337,226 B2
(45) Date of Patent: Jun. 24, 2025

(54) HOME TRAINING SERVICE PROVIDING METHOD AND DISPLAY DEVICE PERFORMING SAME

(71) Applicant: SAMSUNG ELECTRONICS CO., LTD., Suwon-si (KR)

(72) Inventors: Jongin Lee, Suwon-si (KR); Sehyun Kim, Suwon-si (KR); Kilsoo Choi, Suwon-si (KR); Jiwon Park, Suwon-si (KR); Hyunjin Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 18/240,759

(22) Filed: Aug. 31, 2023

(65) Prior Publication Data
US 2023/0405435 A1  Dec. 21, 2023

Related U.S. Application Data

(63) Continuation of application No. PCT/KR2022/003185, filed on Mar. 7, 2022.

(30) Foreign Application Priority Data

Mar. 11, 2021  (KR) .................... 10-2021-0032019

(51) Int. Cl.
*A63B 71/06* (2006.01)
*A63B 24/00* (2006.01)
(Continued)

(52) U.S. Cl.
CPC ...... *A63B 71/0622* (2013.01); *A63B 24/0062* (2013.01); *A63B 24/0075* (2013.01);
(Continued)

(58) Field of Classification Search
CPC ............ A63B 71/0622; A63B 24/0062; A63B 24/0075; A63B 2220/807; H04N 23/90; H04N 23/611; H04N 23/69
See application file for complete search history.

(56) References Cited

U.S. PATENT DOCUMENTS 8,798,363 B2   8/2014  Bhardwaj et al.
10,775,840 B2  9/2020  Lee et al.
(Continued)

FOREIGN PATENT DOCUMENTS

CN   110418205 A   11/2019
JP   2003316510 A  11/2003
(Continued)

OTHER PUBLICATIONS

International Search Report and Written Opinion of the ISA for PCT/KR2022/003185, mailed Jun. 13, 2022, 9 pages.

*Primary Examiner* — Eddy Saint-Vil
(74) *Attorney, Agent, or Firm* — Nixon & Vanderhye, P.C.

(57) ABSTRACT

An example display device includes a display and a processor configured to execute at least one instruction. The processor is configured to control a first camera set at a first angle of view to be activated in response to a request to run an application for providing a home training service, obtain a first image through the activated first camera, control a second camera set at a second angle of view different from the first angle of view to be activated in response to at least one of at least one object included in the first image being identified as a training target object, and provide the home training service based on at least one image obtained through the second camera.

19 Claims, 18 Drawing Sheets

(51) Int. Cl.
*H04N 23/611* (2023.01)
*H04N 23/69* (2023.01)
*H04N 23/90* (2023.01)

(52) U.S. Cl.
CPC ........... *H04N 23/611* (2023.01); *H04N 23/90* (2023.01); *A63B 2220/807* (2013.01); *H04N 23/69* (2023.01)

(56) References Cited

U.S. PATENT DOCUMENTS

| | | | |
|---|---|---|---|
| 10,931,880 B2 | 2/2021 | Byeon et al. | |
| 11,350,033 B2 | 5/2022 | An et al. | |
| 11,717,737 B2 | 8/2023 | Tawiah | |
| 2013/0275313 A1* | 10/2013 | Vahid | G06Q 10/20 |
| | | | 705/305 |
| 2015/0042812 A1* | 2/2015 | Tang | G06V 20/647 |
| | | | 348/157 |
| 2016/0094790 A1* | 3/2016 | Yu | H04N 21/6587 |
| | | | 348/169 |
| 2018/0139374 A1* | 5/2018 | Yu | H04N 21/6587 |
| 2019/0199926 A1* | 6/2019 | An | H04N 23/611 |

FOREIGN PATENT DOCUMENTS

| | | | |
|---|---|---|---|
| JP | 2011505202 A | 2/2011 | |
| JP | 2011151709 A | 8/2011 | |
| JP | 5625417 B2 | 10/2014 | |
| KR | 20170029231 A | 3/2017 | |
| KR | 20170092200 A | 8/2017 | |
| KR | 20180024761 A | 3/2018 | |
| KR | 20200011569 A | 2/2020 | |
| KR | 20200077775 A | 7/2020 | |
| KR | 20200089934 A | 7/2020 | |
| KR | 20200092612 A | 8/2020 | |
| KR | 20200126578 A | 11/2020 | |
| KR | 2367118 B1 | 2/2022 | |

* cited by examiner

FIG. 17
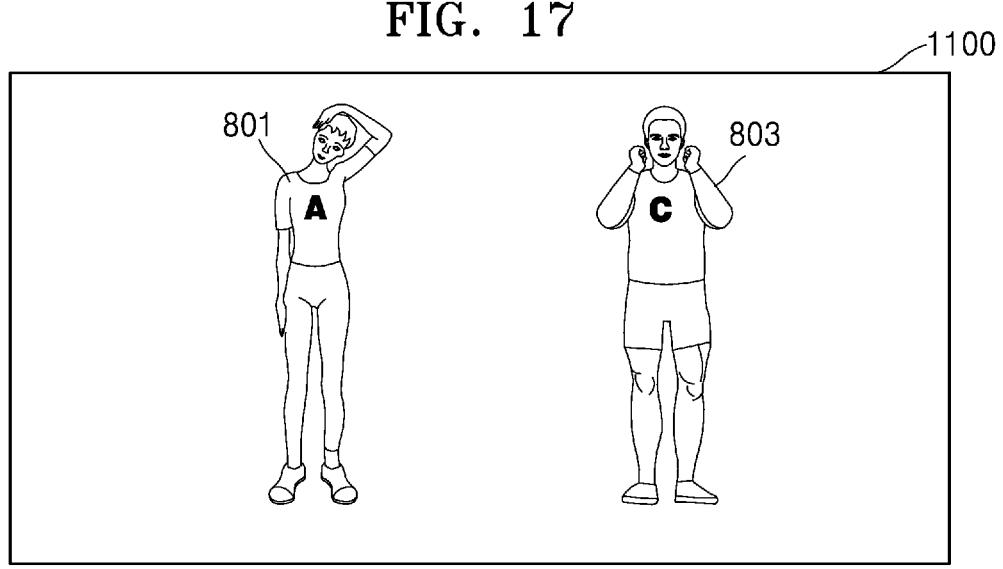
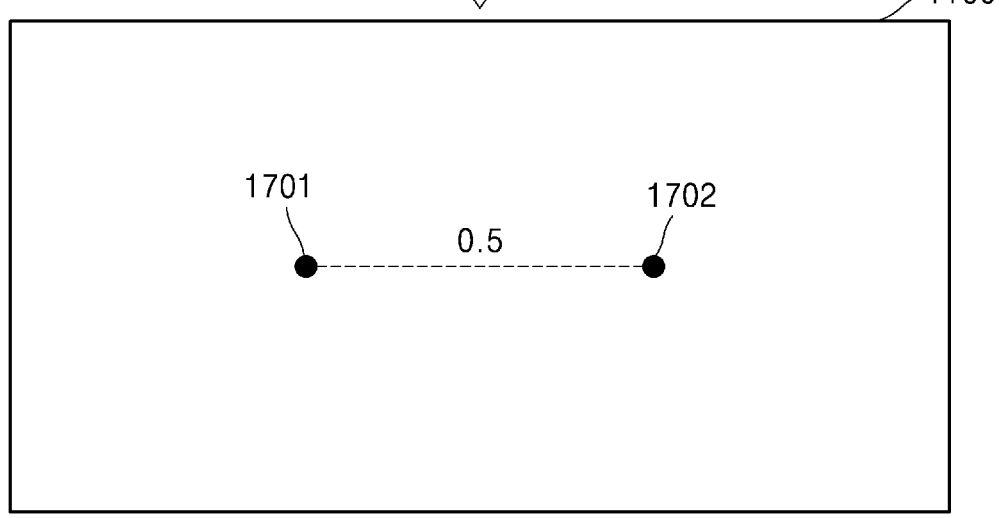
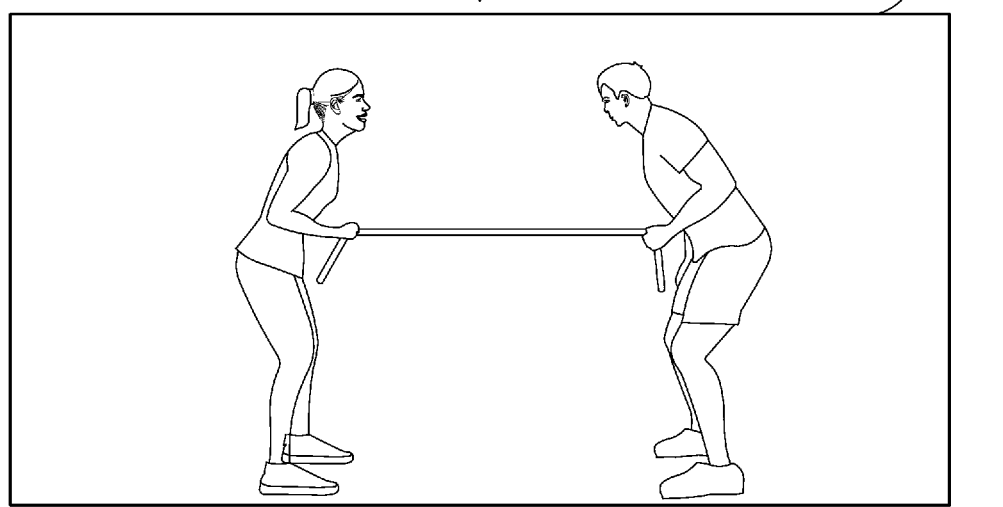

FIG. 18
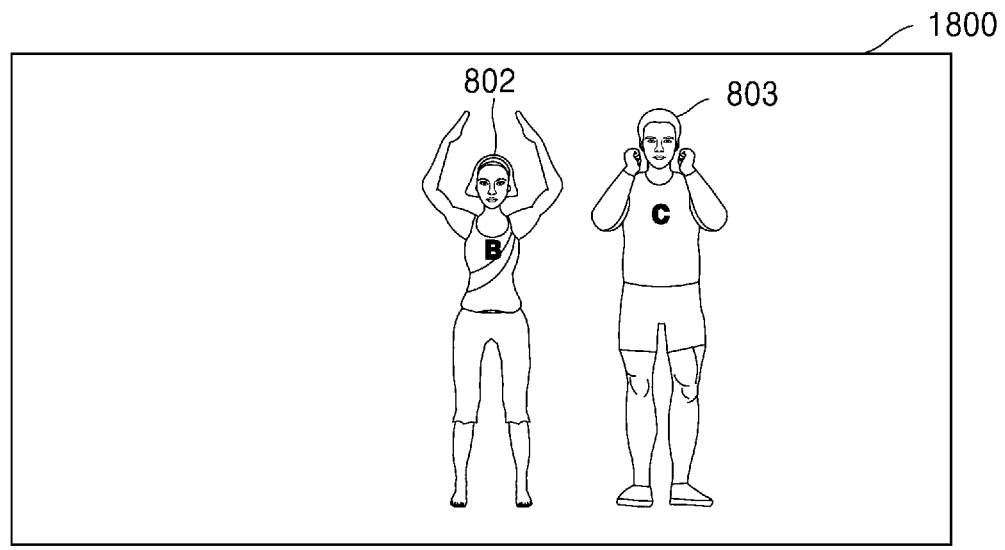
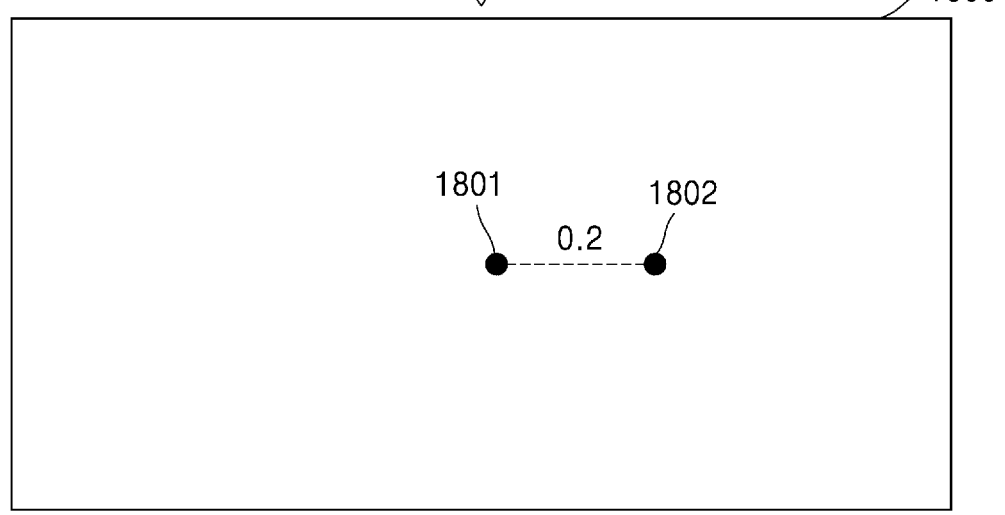
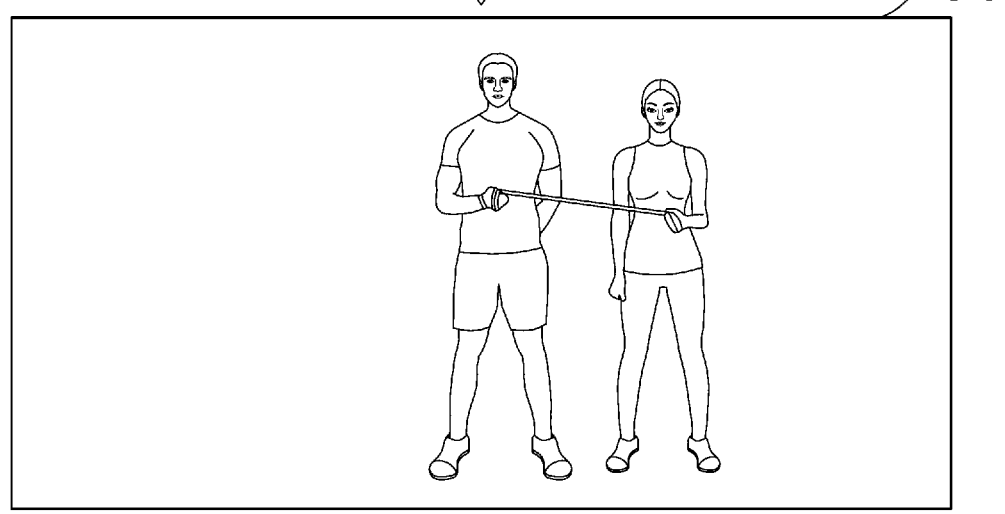

HOME TRAINING SERVICE PROVIDING METHOD AND DISPLAY DEVICE PERFORMING SAME

CROSS-REFERENCE TO RELATED APPLICATIONS

This application is a continuation of PCT/KR2022/003185, designating the United States, filed Mar. 7, 2022, in the Korean Intellectual Property Receiving Office, which claims priority to Korean Patent Application No. 10-2021-0032019, filed on Mar. 11, 2021, in the Korean Intellectual Property Office. The contents of each of these applications are incorporated by reference herein in their entireties.

BACKGROUND

Field

The disclosure relates to a method of providing a home training service and display device for performing the method. More particularly, embodiments of the disclosure relate to a method of providing a home training service to a user who is viewing home training content and following associated moves and a display device for performing the method.

Description of Related Art

With the spread of displays and technology advancement, display devices having various forms and various functions are being developed.

Accordingly, functions conforming to various needs or intentions of consumers may be realized using such display devices.

One of the functions of a display device may be, for example, a function of providing a home training service. A home training service allows a user to follow exercise moves included in content while viewing the content reproduced by the display device.

The content provided in the home training service may include, for example, content for exercise, dance related content, dance lecture content, health care related content, etc. These contents provide moves of an exercise, a dance, or the like, which are continuously performed, and lead a user to follow the moves. The content reproduced or displayed by the display device while the home training service is being provided will be referred to, for example, as home training content.

For example, home training content may, for example, represent an exercise that a user may do in an indoor space (e.g., at home) with a readily available tool or without such extra tools. The user of the display device may easily work out indoors by following exercise moves represented in the home training content while viewing the content.

Furthermore, the home training service provided by the display device may photograph an image of the user and provide information for correcting, coaching and/or guiding exercise moves taken by the user.

Home training services are being developed and provided in a direction of increasing user convenience.

SUMMARY

According to an example embodiment of the disclosure, a display device may include a display; and a processor configured to execute at least one instruction. The processor may be configured to control a first camera set at a first angle of view to be activated in response to a request to execute an application for providing a home training service, obtain a first image through the activated first camera, control a second camera set at a second angle of view different from the first angle of view to be activated in response to at least one of at least one object included in the first image being identified as a training target object, and provide the home training service based on at least one image obtained through the second camera.

In an example embodiment, the first angle of view may be larger than the second angle of view.

In an example embodiment, the first camera may be a wide-angle camera among at least one camera used for the home training service.

In an example embodiment, the display device may further include a communication module (including, e.g., a communication circuit) for communicating with at least one camera. The processor may be configured to identify a camera having a maximum angle of view among the at least one camera as the first camera, and control the first camera to be activated.

In an example embodiment, the display device may further include at least one camera. The processor may be configured to identify a camera having a maximum angle of view among the at least one camera as the first camera, and control the first camera to be activated.

In an example embodiment, the processor may be configured to select a second camera having the second angle of view among at least one camera used for the home training service based on at least one of a location and a number of the identified training target object, and obtain coaching information for the training target object based on at least one image obtained by the second camera.

In an example embodiment, the processor may be configured to change the angle of view of the first camera to the second angle of view based on at least one of a location and a number of the identified training target object, and obtain coaching information for the training target object based on an image obtained by the first camera having the second angle of view while the home training service is being executed.

In an example embodiment, the processor may be configured to identify at least one of the at least one object included in the first image as the training target object based on at least one of a location of the at least one object, a gaze direction of the at least one object, or a distance between the at least one object and the display device.

In an example embodiment, the processor may be configured to select at least one of a plurality of contents based on a number of users corresponding to the identified training target object, and control a content list including the selected at least one content to be output to the display.

In an example embodiment, the processor may be configured to select at least one of a plurality of contents based on a number of users corresponding to the identified training target object, and a formation of the users.

According to an example embodiment of the disclosure, a method of operating a display device for providing a home training service may include controlling a first camera set at a first angle of view to be activated in response to a request to run an application for providing a home training service; obtaining a first image through the activated first camera; controlling a second camera set at a second angle of view different from the first angle of view to be activated in response to at least one of at least one object included in the first image being identified as a training target object; and providing the home training service based on at least one image obtained through the second camera.

In an example embodiment, the first angle of view may have a value larger than the second angle of view.

In an example embodiment, the first camera may be a wide-angle camera among at least one camera used for the home training service.

In an example embodiment, the method may include obtaining coaching information for the training target object based on the at least one image obtained by the second camera; and providing the coaching information to the user while the home training service is being provided.

In an example embodiment, the controlling of the second camera to be activated may include selecting the second camera having the second angle of view among at least one camera used for the home training service based on a location of the identified training target object; and controlling the second camera to be activated.

In an example embodiment, the controlling of the second camera to be activated may include changing the angle of view of the first camera to the second angle of view based on a location of the identified training target object; and controlling the second camera to be activated.

In an example embodiment, the method may further include identifying at least one of the at least one object as the training target object based on at least one of a location of the at least one object included in the first image, a gaze direction of the at least one object, or a distance between the at least one object and the display device.

In an example embodiment, the method may further include selecting at least one of a plurality of contents based on a number of users corresponding to the identified training target object; and controlling a content list including the selected at least one content to be displayed on the display device.

BRIEF DESCRIPTION OF THE DRAWINGS

The above and/or other aspects of the disclosure will be more apparent by describing certain embodiments of the disclosure with reference to the accompanying drawings, in which:

FIG. 17 is a diagram for describing example content provided in an example home training service; and FIG. 18 is a diagram for describing example content provided in an example home training service.

DETAILED DESCRIPTION

Figure 1:
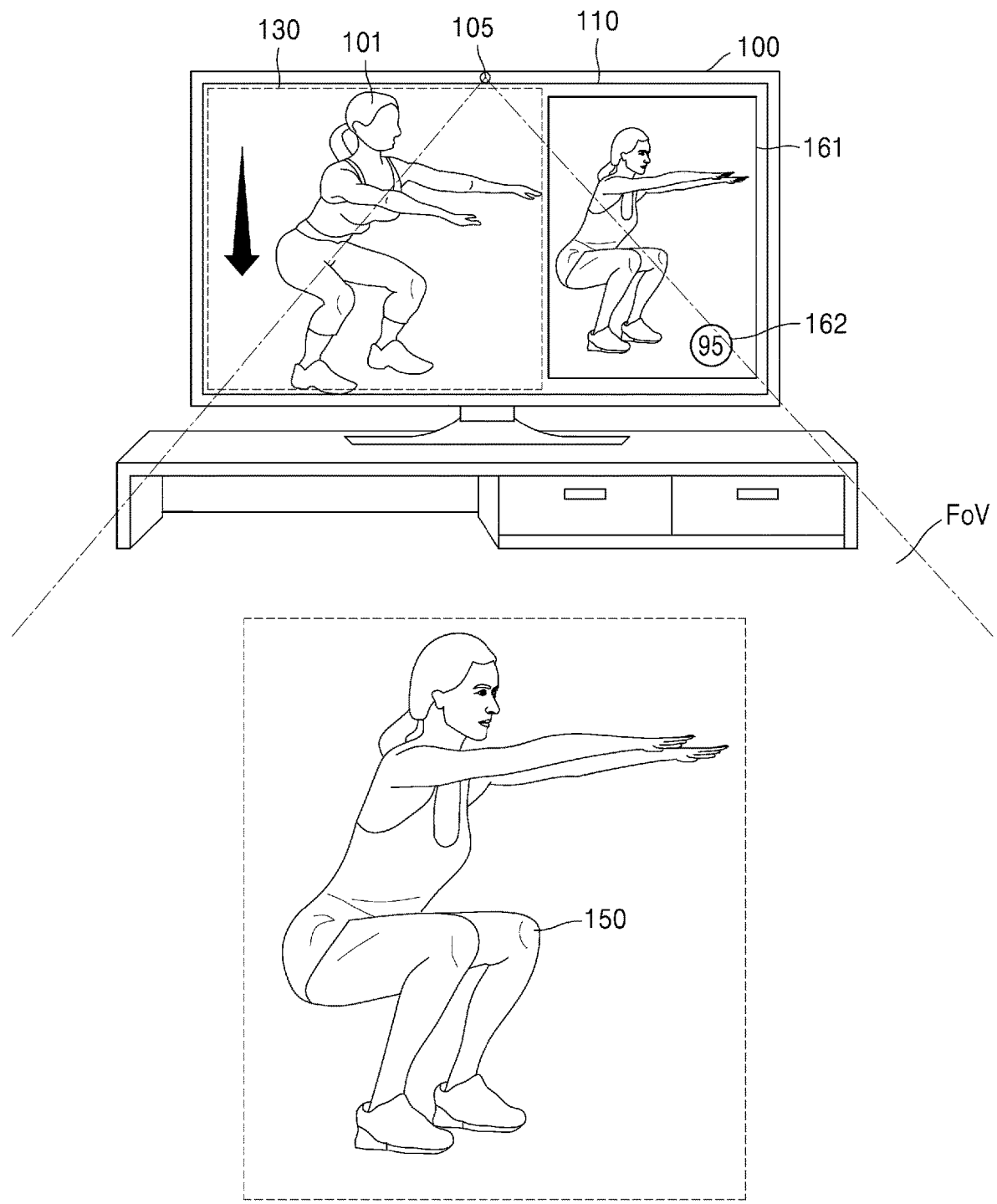
FIG. 1 is a diagram for describing an example home training service provided by an example display device.

Embodiments of the disclosure will now be described with reference to accompanying drawings to assist those of ordinary skill in the art in readily implementing the embodiments. However, the embodiments of the disclosure may be implemented in many different forms, and are not limited to those discussed herein. In the drawings, parts unrelated to the description may be omitted for clarity, and like numerals refer to like elements throughout the specification. Throughout the drawings, like reference numerals denote like elements.

When A is said to "be connected" to B, it may, for example, refer to being "directly connected" to B or "electrically connected" to B with C located between A and B. The term "include (or including)" or "comprise (or comprising)" is inclusive or open-ended and does not exclude additional, unrecited elements or method steps, unless otherwise mentioned.

The phrase "an embodiment" or "some embodiments" or "various embodiments" that appears in the specification does not always refer to the same embodiment.

Various embodiments may be described in terms of functional block components and various processing steps. Some or all of the functional blocks may be implemented by any number of hardware and/or software components configured to perform the specified functions. For example, the functional blocks of the disclosure may be implemented by one or more processor or microprocessors or implemented by circuit elements for performing intended functions. Furthermore, for example, the functional blocks may be implemented in various programing or script languages. The functional blocks may be implemented in algorithms executed on one or more processors. Moreover, the disclosure may employ any number of traditional techniques for electronic configuration, signal processing and/or data processing. The words "module" and "configuration" are used broadly and are not limited to mechanical or physical components.

Connecting lines or members between the elements illustrated in the accompanying drawings are illustratively shown as functional and/or physical connections or circuit connections. In practice, functional, physical, or circuit connections that may be replaced or added may be employed between the elements.

The expression "at least one of A, B and C" refers to one of "A", "B", "C", "A and B", "A and C", "B and C", and "A, B, and C".

In example embodiments of the disclosure, a display device may refer, for example, to any electronic device capable of providing a home training service. The home training service may refer, for example, to a service for allowing a user to follow exercise moves included in content while viewing the content reproduced by the display device. The exercise moves may include, for example, strengthening moves, aerobic moves, stretching moves, dance moves, or other moves related to movement of the user. The content provided in the home training service may include, for example, content for exercise, dance related content, dance lecture content, health care related content, etc. These contents provide moves of an exercise, a dance, or the like, which are continuously performed, and lead the user to follow the moves.

In example embodiments of the disclosure, the display device may, for example, be a television (TV), a digital TV, a smart TV, a digital signage, a digital sign, a smart phone, a tablet personal computer (PC), a personal digital assistant (PDA), a laptop computer, a media player, or the like.

A display device and method for operating the same according to example embodiments of the disclosure will now be described in detail with reference to accompanying drawings. In the accompanying drawings, like elements are denoted by like reference numerals. Also, throughout the specification, the same element is denoted with the same term.

Components of the display device and operations performed by the display device according to example embodiments of the disclosure will now be described in detail with reference to FIGS. 1 to 18.

FIG. 1 is a diagram for describing an example home training service provided by an example display device.

With the development of imaging technology, personal broadcasting, and applications specialized in imaging, a variety of image content and image based services have been provided. The image content and image based services may be provided through the display device. The image content may include video content, which may be reproduced or output through the display device.

For example, the video content may be a content that represents moves related to at least one of dance, gym, exercise treatment, and home training. In another example, the video content may be lecture content that teaches or guides viewers moves related to at least one of dance, gym, exercise treatment, and home training. When the video content is reproduced on the display 110 of the display device 100, the user may move by following the moves represented in the video content.

Referring to FIG. 1, the display device 100 may provide a home training service. The home training service provided by the display device 100 may also be referred to, for example, as a home fitness service, a home gym service, etc. Furthermore, the service for home training may also be referred to, for example, as a 'home training function', a 'home training application', or the like.

While the home training service is being provided, content for leading a user to a move is reproduced. For convenience of reference, the content reproduced with the provision of the home training service may simply be referred to as 'content'.

Referring to FIG. 1, the display device 100 may reproduce the content to provide a home training service. Specifically, the content may be video content that represents squat moves. For example, the content may include content in which a trainer 101 is doing squats. In the above example, the display device 100 may reproduce the video content by displaying or outputting images that represent the squats moves through the display 110 in real time. The user 150 may then view the video content reproduced on the display 110 and follow the squat moves. Although FIG. 1 illustrates a case in which a trainer 101 is doing certain moves, an object such as the trainer 101 may be not only a real human but also text that represents the moves, a virtual object, a virtual avatar, a virtual person, etc.

Furthermore, while the display device 100 is providing the home training service, an image of the user 150 who takes a certain move while viewing the content may be obtained. Specifically, a camera 105 having a field of view FoV included in the display device 100 or electrically connectable to the display device 100 may take a picture(s) of the user 150 who is located in front of the display 110. Accordingly, the camera 105 may obtain an image(s) of the user who is following the squat moves. The display device 100 may then control information for coaching the poses or moves of the user to be output on the display 110 based on the image obtained by the camera 105.

For convenience of explanation, the image output for leading the user to a move, such as the image of the trainer 101 doing a squat move may be referred to as a guide image 130. Furthermore, the information for coaching the poses or moves of the user may be referred to, for example, as coaching information.

For example, the coaching information may be output in data visibly or audibly recognizable to the user. For example, the coaching information may be displayed on a screen to be visibly recognizable to the user. In another example, the coaching information may be output in a voice message through a speaker (not shown) to be audibly recognizable to the user.

For example, when the content is reproduced, the screen output on the display 110 may include a guide image 130 and the coaching information. For example, the guide image 130 may be an image for describing a training movement, and may be an image of the trainer 101 doing a certain move, an image of a virtual object doing a certain move, or an image representing a certain move in text or an image. The coaching information is information for coaching moves of the user 150 who is following the moves while watching the guide image 130, and may include at least one of text and an image. For example, the coaching information may be an image obtained by taking a picture of the user 150 who is following a certain move, information indicating an accuracy in the pose or move of the user 150 who is following the certain move (scores, marks of inaccurate part, etc.), or an image representing an indication or instruction about a part to be corrected of the pose of the user 150 who is following the certain move.

For example, the coaching information may be an image 161 indicating a score 162 that represents accuracy of the pose of the user 150 on the captured image of the user 150. The coaching information may include a message like 'bad', 'good', 'excellent', etc., which gives relative expression of the pose. The coaching information may include a text message or a voice message such as 'bend your left knee further, please'.

In an embodiment of the disclosure, the display device 100 may obtain an image of the user 150 and output the coaching information on the display based on the obtained image while providing the home training service.

Figure 2:
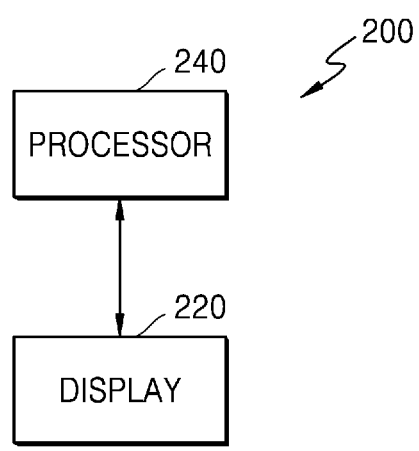
FIG. 2 is a block diagram illustrating an example display device, according to various embodiments.

FIG. 2 is a block diagram illustrating an example display device, according to various embodiments. A display device 200 shown in FIG. 2 corresponds to the display device 100 as described above in FIG. 1, so the overlapping description will not be repeated.

In an example embodiment of the disclosure, the display device 200 may include any electronic device that visually displays content for home training.

Referring to FIG. 2, the display device 200 includes a display 220 and a processor 240 for executing at least one instruction.

Specifically, according to an example embodiment of the disclosure, the processor 240 (including, e.g., processing circuitry) included in the display device 200 executes at least one instruction to control a camera set at a first angle of view to be activated in response to a request to run an application for providing a home training service, obtain a first image through the activated camera, control a second camera set at a second angle of view different from the first angle of view to be activated in response to at least one of at least one object included in the first image being identified as a training target object, and provide the home training service based on at least one image obtained through the second camera.

For convenience of explanation, the camera having the first angle of view may be referred to, for example, as a first camera. The camera having the second angle of view may be referred to, for example, as the second camera. The first camera and the second camera refer to no particular cameras but cameras having certain view angles or set at the certain view angles. For example, when there is a camera having an angle of view variable within a certain range, the camera on an occasion when the angle of view is set to the first angle of view may be referred to as the first camera, and the camera on an occasion when the angle of view is set to the second angle of view may be referred to as the second camera. In another example, when there are a plurality of cameras having different angles of view, a camera having the first angle of view or which may be set at the first angle of view among the plurality of cameras may be referred to as the first camera, and a camera having the second angle of view or which may be set at the second angle of view among the plurality of cameras may be referred to as the second camera.

In an example embodiment of the disclosure, the first angle of view may have a value greater than the second angle of view.

The first camera (not shown in FIG. 2) may be a camera included in the display device 200, or an external device physically separated from the display device 200, which is an external camera electrically connectable to the display device 200. A case in which the display device 200 includes the first camera will be described in connection with FIG. 3, and a case in which the display device 200 does not include the first camera will be described in connection with FIG. 4.

In an example embodiment of the disclosure, a home training service may be provided through a function menu, a program, or an application included in the display device 200.

For example, the home training service may be performed through a home training application. The home training application may be implemented with at least one instruction or a program that executes the home training service.

For example, the home training application may be installed during the manufacture of the display device 200. Specifically, when the display device 200 is manufactured, the home training application may be installed and stored in the processor 240 or an internal memory (not shown) of the display device 200.

In another example, the home training application may be externally manufactured and/or distributed. Specifically, the home training application may be distributed through an application store (e.g., SAMSUNG Galaxy store™, Play-store™, etc.) or directly between two user equipments (e.g., smart phones and/or smart TVs), or distributed online (e.g., downloaded or uploaded from a server). In a case of online distribution, it may be distributed through a server of the manufacturer of the display device 200, a server of the application store, or a relay server.

Accordingly, the display device 200 may store the home training application. For example, the home training application may be stored in the processor 240, or may be stored in a separate memory (not shown) included in the display device 200.

The home training application may self-store the content for home training or receive the content from an external server, an Internet server, or the like. Accordingly, the home training application may control the content self-stored after being executed or received in real time to be reproduced by the display 220.

After being executed, the home training application may obtain an image of the user who is doing home training, and generate and output information for coaching poses of the user who is doing the home training.

For convenience of naming and explanation, the home training application may be referred to, for example, as an application.

In an example embodiment of the disclosure, the application for providing a home training service (specifically, the home training application) may be executed at the request or setting of the user. For example, the display device 200 may receive a user input requesting execution of the application. Alternatively, the processor 240 may set the application to be started at an appointed time and date (e.g., 8 a.m., every day) according to its own settings or settings of the user. The request for execution of the application according to user input or settings may be collectively referred to, for example, as an application execution request.

In an example embodiment of the disclosure, the processor 240 may control the camera used to provide the home training service to be activated in response to reception of the application execution request. Specifically, in response to the application execution request, the processor 240 may identify a camera having the first angle of view and control the identified at least one camera to be activated. The camera having the first angle of view may be referred to, for example, as the first camera. Operations of the identifying and activating of the first camera will be described in detail with reference to FIGS. 7, 8, 9, and 10.

In an example embodiment of the disclosure, the processor 240 controls an intended operation to be performed by executing at least one instruction. The processor 240 may control a general or overall operation of the display device 200. The processor 240 may control the other components included in the display device 200 to perform a certain operation(s).

Specifically, the processor 240 may include an internal memory (not shown) and at least one processor (not shown) for executing at least one stored program. The internal memory of the processor 240 may store one or more instructions. The processor 240 may perform a certain operation(s) by executing at least one of the one or more instructions stored in the internal memory. The processor 240 performing the certain operation(s) may include not only an occasion when the processor 240 performs the certain operation(s) by itself but also an occasion when the processor 240 controls another component included in the display device 200 or another device (e.g., an external camera) separated from the display device 200 to perform the certain operation(s).

Specifically, the display 220 visually outputs an image. For example, the display 220 may display an image corresponding to video data through a display panel (not shown) included in the display 220 for the user to visually recognize video content. Specifically, the video data that forms the content may include a plurality of image frames, and the display 220 may reproduce the video content by displaying the plurality of image frames successively under the control of the processor 240.

The processor 240 may include a random access memory (RAM) (not shown) for storing a signal or data input from outside of the display device 200 and/or for use as a storage area corresponding to various tasks performed on the display device 200, a read only memory (ROM) (not shown) for storing a control program and/or a plurality of instructions to control the display device 200, and at least one processor (not shown).

The processor 240 may also include a graphic processing unit (GPU) (not shown) for graphic processing corresponding to video. The processor 240 may be implemented as a system on chip (SoC) in which a core (not shown) and the GPU are integrated. The processor 240 may include a single core or multiple cores. For example, the processor 240 may include a dual-core, a triple-core, a quad-core, a hexa-core, an octa-core, a deca-core, a dodeca-core, a hexa-dash-vale core, etc.

Figure 3:
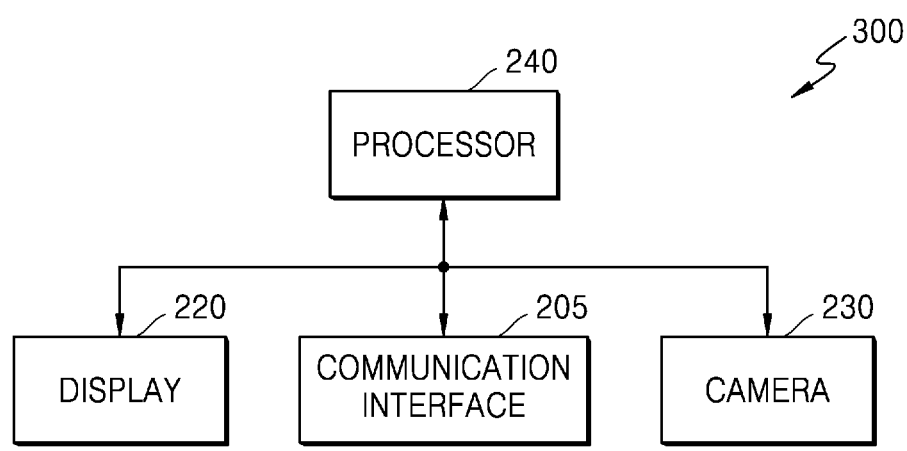
FIG. 3 is a block diagram illustrating an example display device, according to various embodiments.

FIG. 3 is a block diagram illustrating an example display device, according to various embodiments.

Referring to FIG. 3, a display device 300 shown in FIG. 3 may correspond to the display device 200 shown in FIG. 2. Hence, what is described above in connection with FIG. 2 will not be repeated in describing the display device 300.

Referring to FIG. 3, compared with the display device 200 shown in FIG. 2, the display device 300 may further include at least one of a communication interface 205 or a camera 230.

Specifically, the communication interface 205 (including, e.g., a communication circuit) may perform communication with at least one external device (not shown) over a wired or wireless communication network. The external device may be, for example, a mobile device including at least one camera, an external camera, other electronic devices including at least one camera, etc.

Specifically, the communication interface 205 may include at least one wireless communication module, a wireless communication circuit, or a wireless communication device for wirelessly communicating with an external device.

For example, the communication interface 205 may include at least one communication module (not shown) to perform communication according to a communication standard such as Bluetooth, wireless fidelity (Wi-Fi), Bluetooth low energy (BLE), near field communication/radio frequency identification (RFID), Wi-Fi direct, ultra wideband (UWB) or Zigbee. Furthermore, the communication interface 205 may include a communication module (not shown) to perform communication with a server (not shown) for supporting long-range communication according to a long-range communication standard. For example, the communication interface 205 may include a communication module (not shown) that performs communication over a network for Internet communication. The communication interface 205 may include a communication module (not shown) for performing communication over a communication network conforming to a communication standard such as 3G, 4G, 5G and/or 6G.

The communication interface 205 may include at least one port (not shown) to connect to an external device through a cable to wiredly communicate with an external device (e.g., a scanner). For example, the communication interface 205 may include at least one of a high-definition multimedia interface (HDMI) port, a component jack, a PC port and a universal serial bus (USB) port. Accordingly, the communication interface 205 may communicate with an external device wiredly connected through at least one port (not shown).

The camera 230 may obtain at least one image. The camera 230 is shown in FIG. 3 as being a single camera, but may include a plurality of cameras. Specifically, the camera 230 may refer to at least one camera. More specifically, the camera 230 may include at least one camera used for the home training service.

For example, the camera 230 may include a plurality of cameras having different angles of view. In this case, having different angles of view may refer, for example, to viewing angles of different cameras being different from each other by setting the viewing angles differently. Alternatively, having different angles of view may refer, for example, to ranges of the viewing angles of two different cameras being different from each other. For example, the camera 230 may include at least one of a standard camera (e.g., a camera having an angle of view ranging from 40 to 60 degrees), a telecamera (e.g., a camera having an angle of view of 40 or less degrees), a wide-angle camera (e.g., a camera having an angle of view ranging from 60 to 80 degrees), an optically zoomable camera (e.g., a camera having an angle of view that is adjustable within a range of 60 to 80 degrees by physically adjusting the lens of the camera), and a digitally zoomable camera (e.g., a camera able to digitally adjust the capturing range). The standard camera may be, for example, a camera set to 1× zoom, which may be referred to as a normal camera. There may be a wide variety of telecameras, wide-angle cameras, optically zoomable cameras and digitally zoomable cameras depending on designs and/or product specifications. Functions and detailed configurations of the optical zoom and digital zoom are well-known, so a description thereof is omitted.

In another example, the camera 230 may include one camera having an adjustable angle of view. The angle of view may correspond to, for example, a range to capture an image obtained by the camera 230. Adjusting the angle of view may refer, for example, to adjusting a focal distance of the camera 230.

A case in which the display device 300 includes the display 220, the camera 230, the processor 240 and the communication interface 205 according to an embodiment of the disclosure will now be described as an example.

For example, the camera 230 may include a plurality of cameras having different angles of view. In this case, the processor 240 may control the first camera set at the first angle of view among the plurality of cameras to be activated in response to the application execution request. For example, the first angle of view may have a greater value than an angle of view of a camera expressing 1× zoom. The first angle of view may be an angle of view of a wide-angle camera. For example, the first angle of view may be set to a value between 60 and 80 degrees corresponding to the wide-angle camera. In another example, the first angle of view may be a maximum angle of view among the angles of view of a plurality of cameras included in the camera 230.

In an example embodiment of the disclosure, the first camera may be a wide-angle camera among the plurality of cameras. For example, the first camera may be a camera having a maximum angle of view among the plurality of cameras.

The second angle of view may have a value smaller than the first angle of view.

In another example, the camera 230 may include at least one camera having an angle of view that is adjustable within a set range. In this case, the processor 240 may control the first camera that may be set at the first angle of view to be activated among the at least one camera in response to the application execution request. For example, when the camera 230 includes a wide-angle camera having an angle of view adjustable within a range between 60 and 80 degrees, the processor 240 may change the angle of view of the wide-angle camera to its maximum value in response to the application execution request. The processor 240 may control the first camera, a wide-angle camera having a changed maximum angle of view, to be activated.

When the camera 230 includes a plurality of cameras having different angles of view, the processor 240 may identify the first camera having the angle of view of the wide-angle camera among the plurality of cameras, and change the angle of view of the first camera to the maximum angle of view. When the camera 230 includes a plurality of cameras having different angles of view, the processor 240 may identify the first camera having the maximum angle of view among the plurality of cameras, and control the identified first camera to be activated.

For example, when the camera 230 includes a single camera (specifically, the first camera), the angle of view of the first camera may be changed to the maximum angle of view.

In another example, when the camera 230 includes a wide-angle camera having an angle of view of 80 degrees, the processor 240 may control the wide-angle camera (specifically, the first camera) to be activated in response to the application execution request.

In another example, the camera 230 may include a single camera (specifically, the first camera) having an angle of view that is adjustable within a set range. In this case, the processor 240 may change the angle of view of the first camera to the maximum angle of view and control the first camera having the changed maximum angle of view to be activated, in response to the application execution request.

The processor 240 may control the activated camera 230 (e.g., the activated first camera) to obtain a first image.

The first image may be, for example, an image used to identify a training target object. Specifically, the first image may be an image used to identify a user who is going to follow training moves according to the home training before the home training content is reproduced. For example, the first image may be an image obtained by the camera 230 photographing the front of the display device 300. Accordingly, the first image may be an image including at least one user located in front of the display device 300 as an object. The first image may be an image that represents a gesture, a motion, a pose and/or a movement of each of the at least one user. For convenience of explanation, the gesture, motion, pose and/or movement may be collectively referred to, for example, as the gesture.

The processor 240 may identify at least one of the at least one object included in the first image as the training target object, and provide a home training service for the identified training target object. The training target object may refer, for example, to a user who is going to exercise by following exercise poses included in content while viewing the content.

The processor 240 may control a second camera set at a second angle of view different from the first angle of view to be activated in response to at least one of the at least one object included in the first image being identified as the training target object. The processor 240 may provide the home training service based on at least one image obtained through the second camera.

For example, the processor 240 may obtain coaching information for the training target object based on at least one image obtained by the second camera. The processor 240 may provide the coaching information to the user while the home training service is being provided. For example, the processor 240 may output the coaching information to be visually or audibly recognized by the user while the home training service is being provided.

For example, the second angle of view may have a value smaller than the first angle of view. For example, when the first angle of view is an angle of view of a wide-angle camera, the second angle of view may be an angle of view of a standard camera (or normal camera) or telecamera.

In another example, when the first angle of view corresponds to a maximum value of the angle of view of the camera, the second angle of view may refer to an angle of view with which only the identified training target object is photographed in a region of interest or a field of view (FOV) area.

The second angle of view will be described in detail with reference to FIGS. 11, 12, 13, and 14.

Although an occasion when the camera 230 is included in the display device 300 is described and illustrated in FIG. 3, the camera 230 may be provided as a separate device physically distinguished from the display device 300. This will be described in detail with reference to FIG. 4.

Figure 4:
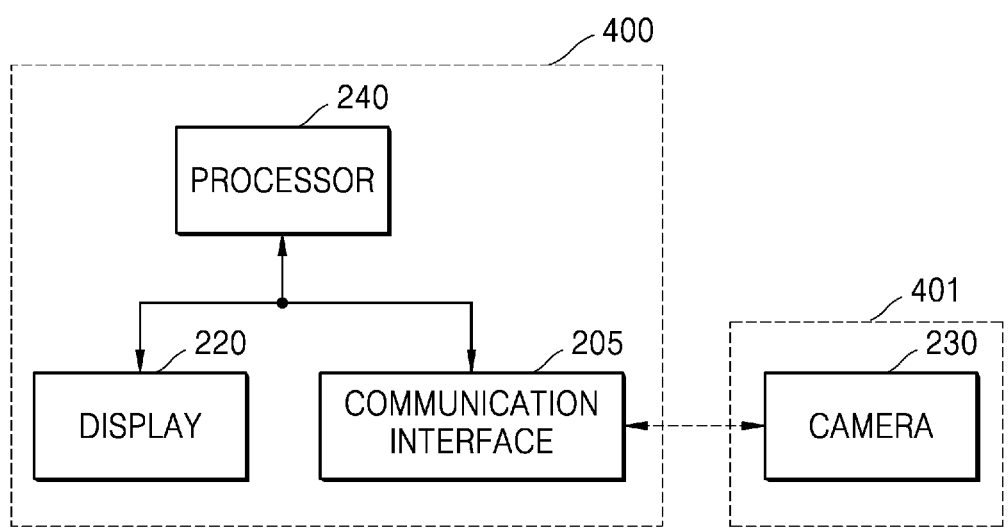
FIG. 4 is a block diagram illustrating an example display device, according to various embodiments.

FIG. 4 is a block diagram illustrating an example display device, according to various embodiments. Referring to FIG. 4, a display device 400 shown in FIG. 4 may correspond to the display device 200 shown in FIG. 2. The communication interface 205 and the camera 230 shown in FIG. 4 may also correspond to the communication interface 205 and the camera 230 shown in FIG. 3, respectively. Hence, what is described above in connection with FIGS. 2 and 3 will not be repeated in describing the display device 300.

Although an occasion when the camera 230 is included in the display device 300 is illustrated and described in FIG. 3, the display device 400 shown in FIG. 4 does not include the camera 230, and the camera 230 may be included in a separate device 401 distinguished from (or external to) the display device 400. Specifically, the device 401 may be an external camera device, a smart phone, a tablet PC, a PDA, a laptop computer, a media player, etc. The camera 230 may be arranged or installed to photograph a space in front of the display device 100 as the camera 105 shown in FIG. 1.

The device 401 may, for example, be electrically connected to the display device 400 through the communication interface 205. Specifically, the device 401 may include a communication interface (not shown) and transmit or receive data and/or signals to or from the display device 400 through the communication interface.

Specifically, the display device 400 may receive an image obtained by the camera 230 through the communication interface 205. As described above in FIG. 3, the camera 230 may include at least one camera, and the at least one camera may have different angles of view.

In an example embodiment of the disclosure, the processor 240 may control the first camera having an angle of view set to the first angle of view to be activated and control the first image to be obtained through the activated first camera, in response to a request to execute an application that provides the home training service. For example, the processor 240 may create a command to control the first camera having an angle of view set to the first angle of view to be activated, in response to the application execution request. The command created by the processor 240 may be transmitted to the device 401 through the communication interface 205. The device 401 may then identify the first camera having the angle of view set to the first angle of view and activate the identified first camera based on the received command. Subsequently, the first camera included in the camera 230 may obtain the first image while in the activated state.

As described above, the processor 240 may transmit a request or command to the device 401 through the communication interface 205, and the device 401 may perform an operation corresponding to the received request or command. The device 401 may transmit at least one image obtained by the camera 230 to the display device 400. Accordingly, the processor 240 of the display device 400 may obtain at least one image (e.g., the first image) obtained by the camera 230.

Figure 5:
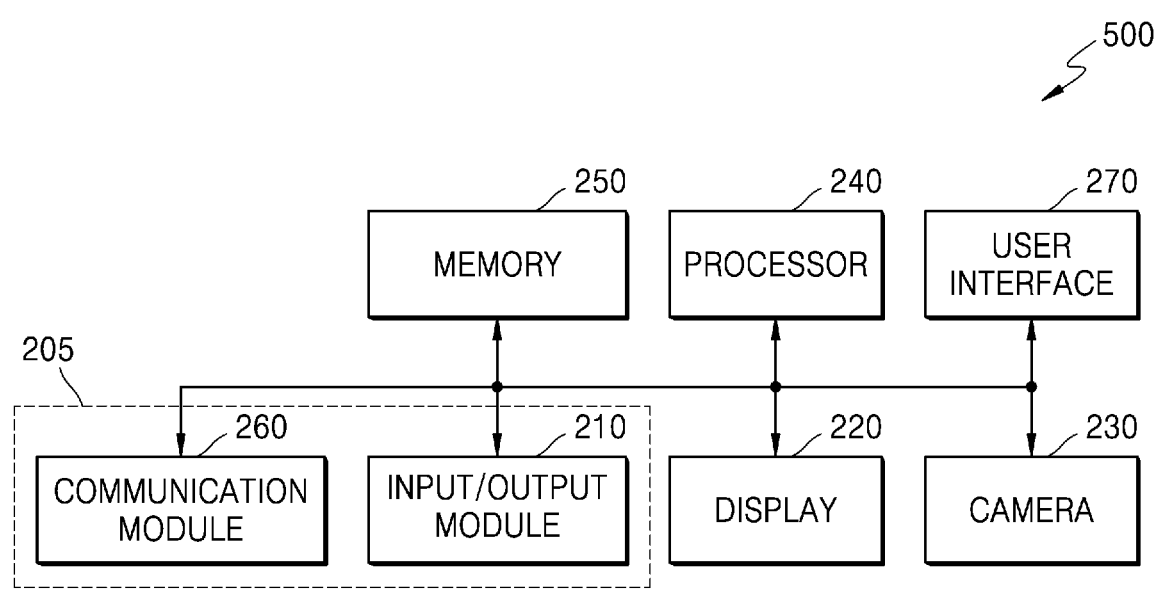
FIG. 5 is a block diagram illustrating an example display device, according to various embodiments.

FIG. 5 is a block diagram illustrating an example display device, according to various embodiments.

The display device 500 shown in FIG. 5 may correspond to the display device 200 shown in FIG. 2. The communication interface 205 and the camera 230 shown in FIG. 5 may also correspond to the communication interface 205 and the camera 230 shown in FIG. 3 and FIG. 4, respectively. Hence, what is described above in connection with FIGS. 2, 3, and 4 will not be repeated in describing the display device 500.

Referring to FIG. 5, compared with the display device 200 shown in FIG. 2, the display device 500 may further include at least one of the communication interface 205, the camera 230, a memory 250 and a user interface 270.

The memory 250 may store at least one instruction. The memory 250 may store the at least one instruction to be executed by the processor 240. The memory 250 may also store at least one program to be executed by the processor 240. The memory 250 may also store an application for providing a certain function, a certain operation and/or a certain service. In an embodiment of the disclosure, the memory 250 may store a home training application.

Furthermore, the memory 250 may store information or data used for operation of the display device 500. The memory 250 may also store content that may be reproduced by the display device 500. In an embodiment of the disclosure, the memory 250 may store at least one image (e.g., the first image) obtained by the camera 230.

Specifically, the memory 250 may include at least one type of storage medium including a flash memory, a hard disk, a multimedia card micro type memory, a card type memory (e.g., SD or XD memory), a RAM, a Static Random Access Memory (SRAM), a ROM, an Electrically Erasable Programmable Read-Only Memory (EEPROM), a Programmable Read-Only Memory (PROM), a magnetic memory, a magnetic disk, or an optical disk.

The communication interface 205 may include at least one of at least one communication module and at least one port for transmitting or receiving data to or from an external device. Specifically, the communication interface 205 may include a communication module 260 and an input/output module 210. For example, the communication module 260 may communicate with an external device (e.g., the device 401 as described in FIG. 4, a server for distributing an application, a server for providing a content for home training, etc.).

The communication module 260 (including, e.g., a communication circuit) communicates with an external device (not shown) over at least one wired or wireless communication network. In an example embodiment of the disclosure, the communication module 260 may communicate with the external device. The external device may be a server (not shown), and the communication module 260 may communicate with the server. The server may be a content providing server, an Internet server, etc., for providing content. The server may analyze, process, and/or handle an image. The server may also manufacture and/or distribute an application.

Specifically, the communication module 260 may have a form that includes at least one communication module, a communication circuit, etc., and may transmit or receive data to or from an external device through the communication module and/or the communication circuit.

Specifically, the communication module 260 may include at least one communication module (not shown) to perform communication according to a communication standard such as Bluetooth, wireless fidelity (Wi-Fi), Bluetooth low energy (BLE), near field communication/radio frequency identification (RFID), Wi-Fi direct, ultra wideband (UWB) or Zigbee.

Furthermore, the communication module 260 may further include a communication module (not shown) to perform communication with a server (not shown) for supporting long-range communication according to a long-range communication standard. Specifically, the communication module 260 may include a communication module (not shown) that performs communication over a network for Internet communication. Moreover, the communication module 260 may include a communication network according to a communication standard such as 3G, 4G and/or 5G.

The communication module 260 may further include a communication module, e.g., an infrared (IR) communication module, that may receive a control command from a remote controller (not shown) located nearby. In this case, the communication module 260 may receive a control command from the remote controller. For example, the control command received from the remote controller may include a turn-on or turn-off command, a signal for requesting execution of the home training application, etc.

The input/output module 210 (including, e.g., an input/output circuit) may include one of an HDMI port (not shown), a component jack (not shown), a PC port (not shown), and a USB port (not shown). The input/output module 210 may also include a combination of the HDMI port, the component jack, the PC port, and the USB port. In this case, the input/output module 210 may receive video data to be played on the display device 500 directly through the HDMI port, the component jack, the PC port, or the USB port.

The user interface 270 (including, e.g., a user interface circuit) may receive a user input to control the display device 500. The user interface 270 may include a user input device including a touch panel for detecting a touch of the user, a button for receiving a push operation of the user, a wheel for receiving a turning manipulation of the user, a keyboard, a dome switch, etc., without being limited thereto.

The user interface 270 may also include a voice recognition device (not shown) for voice recognition. For example, the voice recognition device may be a microphone, and may receive a voice command or voice request of the user. Accordingly, the processor 240 may control an operation corresponding to the voice command or voice request to be performed.

The user interface 270 may include a motion detection sensor (not shown). For example, the motion detection sensor (not shown) may detect a motion of the display device 500, and receive the detected motion as a user input. The aforementioned voice recognition device (not shown) and the motion detection sensor (not shown) may, for example, not be integrated in the user interface 270 but may be included as modules separate from the user interface 270 in the display device 500.

In an example embodiment of the disclosure, the user interface 270 may receive a user input corresponding to a request to execute the home training application from the user. On receiving the user input, the processor 240 may run the home training application to perform operations according to an example embodiment of the disclosure (e.g., an operation of identifying and activating the first camera, an operation of obtaining the first image, and an operation of identifying a training target).

Figure 6:
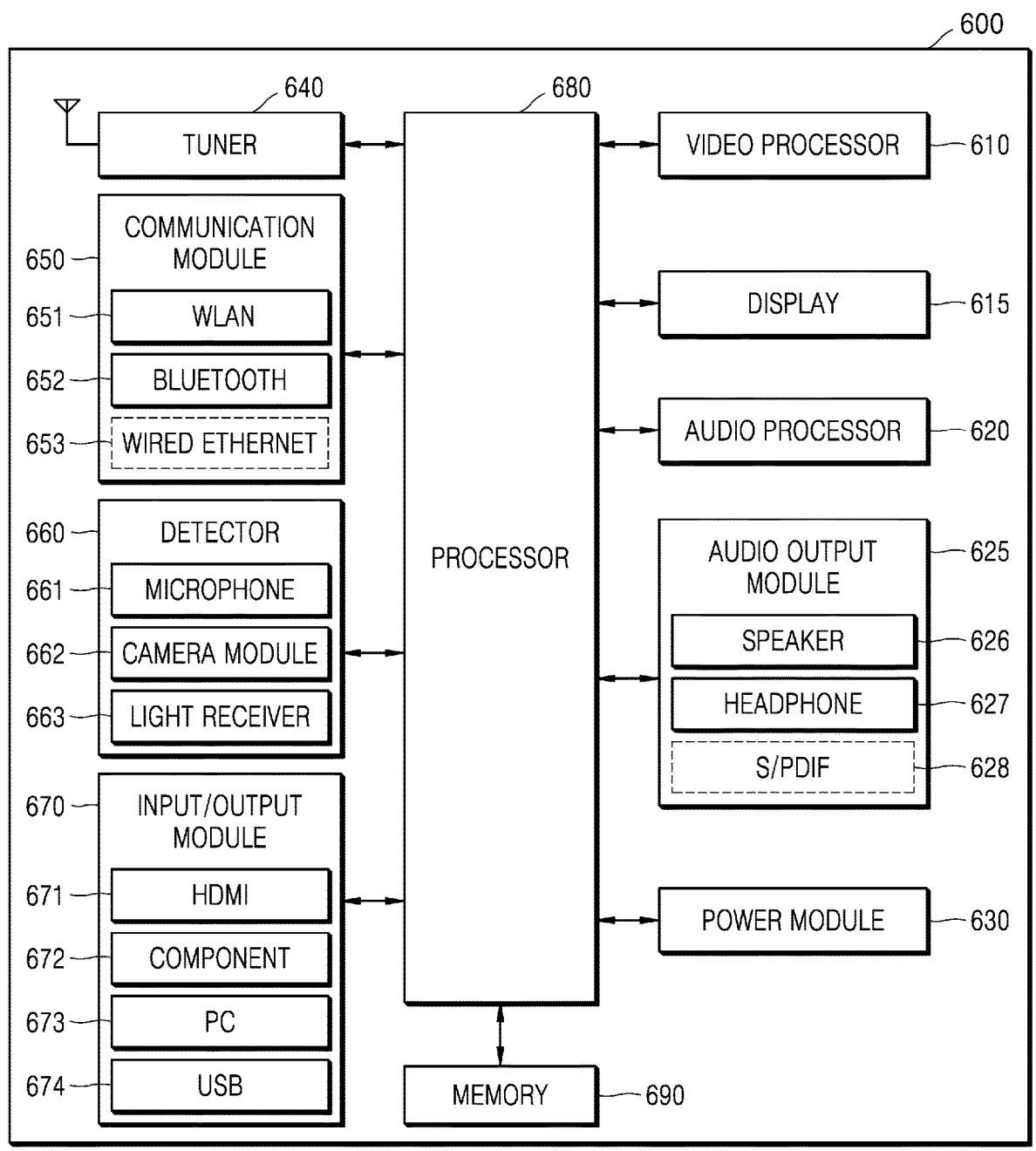
FIG. 6 is a block diagram illustrating an example display device, according to various embodiments.

FIG. 6 is a block diagram illustrating an example display device, according to various embodiments. A display device 600 shown in FIG. 6 may correspond to the display device 100, 200, 300, 400 or 500 shown in FIGS. 1, 2, 3, 4, and 5. Hence, what is described above in connection with FIGS. 1, 2, 3, 4, and 5 will not be repeated in describing the display device 600.

Referring to FIG. 6, the display device 600 includes a video processor 610, a display 615, an audio processor 620, an audio output module 625, a power module 630, a tuner 640, a communication module 650, a detector 660, an input/output module 670, a processor 680 and a memory 690.

The communication module 650, the display 615, the camera module 662, the input/output module 670, the processor 680 and the memory 690 of the display device 600 may correspond to the communication module 260, the display 220, the camera 230, the input/output module 210, the processor 240 and the memory 250 as described in FIGS. 2, 3, 4, and 5. Hence, what is described above in connection with FIGS. 2, 3, 4, and will not be repeated in describing the display device 600.

The video processor 610 processes video data received by the display device 600. The video processor 610 may perform various image processes such as, for example, decoding, scaling, noise filtering, frame rate conversion, resolution conversion, etc., on the video data.

The display 615 displays a video included in a broadcast signal received through the tuner 640 on the screen, under the control of the processor 680. Furthermore, the display 615 may display content, e.g., a video, received through the communication module 650 or the input/output module 670.

The display 615 may also output an image stored in the memory 690, under the control of the processor 680. The display 615 may display a voice user interface (UI) (e.g., including a voice instruction guide) for performing a voice recognition task corresponding to voice recognition or a motion UI (e.g., including a user motion guide for motion recognition) for performing a motion recognition task corresponding to motion recognition.

In an example embodiment of the disclosure, the display 615 may display content reproduced when the home training application is executed.

The audio processor 620 processes audio data. The audio processor 620 may perform various processes such as, for example, decoding, amplification, noise filtering, etc., on the audio data. The audio processor 620 may include a plurality of audio processing modules to process audio corresponding to a plurality of contents.

The audio output module 625 outputs audio included in a broadcast signal received through the tuner 640 under the control of the processor 680. The audio output module 625 may output audio, e.g., voice or sound, received through the communication module 650 or the input/output module 670. Furthermore, the audio output module 625 may output audio stored in the memory 690 under the control of the processor 680. The audio output module 625 may include at least one of a speaker 626, a headphone output terminal 627 or a Sony/Phillips digital interface (S/PDIF) output terminal 628. The audio output 625 may include a combination of the speaker 626, the headphone output terminal 627 and the S/PDIF output terminal 628.

The power module 630 supplies power received from an external power source to the components 610 to 690 in the display device 600 under the control of the processor 680. Furthermore, the power module 630 may supply power output from one or two or more batteries (not shown) located in the display device 600 to the internal components 610 to 690 under the control of the processor 680.

The tuner 640 may tune to and select a frequency of a channel that the display device 600 intends to receive among a plurality of radio components through, for example, amplification, mixing, resonance of broadcast signals received wiredly or wirelessly. The broadcast signal may include, for example, audio, video, and additional information, e.g., electronic program guide (EPG).

The tuner 640 may receive a broadcast signal in a frequency band corresponding to a channel number (e.g., cable channel no. 506) according to a user input (for example, a control signal, e.g., a channel number input, a channel up/down input and a channel input on an EPG screen received from an external control device (not shown), e.g., a remote controller).

The tuner 640 may receive broadcast signals from various sources such as terrestrial broadcasters, cable broadcasters, satellite broadcasters, Internet broadcasters, etc. The tuner 640 may also receive broadcast signals from a source such as an analog broadcaster or a digital broadcaster. A broadcast signal received through the tuner 640 is decoded (e.g., audio decoding, video decoding or additional information decoding) and divided into audio, video and/or additional information. The divided audio, video and/or additional information may be stored in the memory 690 under the control of the processor 680.

There may be one or multiple tuners 640 in the display device 600. When the tuner 640 is as a plurality of tuners in an example embodiment, a plurality of broadcast signals may be output in a plurality of windows that make up a multi-window screen provided on the display 615.

The tuner 640 may be implemented as an all-in-one device with the display device 600 or implemented in a separate device (e.g., a set-top box (not shown), a tuner (not shown) connected to the input/output module 670) having a tuner electrically connected to the display device 600.

The communication module 650 may connect the display device 600 to an external device (e.g., an external camera, a smart phone, an audio device, etc.) under the control of the processor 680. The processor 680 may transmit or receive content to or from an external device connected through the communication module 650, download an application from the external device, or browse the web for the content. Specifically, the communication module 650 may access a network to receive content from an external device (not shown).

As described above, the communication module 650 may include at least one of a short-range communication module (not shown), a wired communication module (not shown), and a mobile communication module (not shown).

In FIG. 6, a case in which the communication module 650 includes one of a WLAN 651, a Bluetooth communication module 652, and a wired Ethernet 653 is shown as an example.

The communication module 650 may include a module combination including one or more of the WLAN 651, the Bluetooth communication module 652 and the wired Ethernet 653. The communication module 650 may receive a control signal of a control device (not shown) under the control of the processor 680. The control signal may be implemented in a Bluetooth type, a radio frequency (RF) signal type or a Wi-Fi type.

The communication module 650 may further include a short-range communication module other than Bluetooth (e.g., near field communication (NFC) module (not shown) or an extra BLE module (not shown)).

The detector 660 detects the user's voice, the user's image or the user's interaction.

In an example embodiment of the disclosure, the detector 660 may obtain data to identify the user's gesture. Specifically, the detector 660 may include the camera module 662 and use the camera module 662 to obtain data for identifying the user's gesture (e.g., an image representing the user's gesture). The detector 660 may further include at least one of a microphone 661 and a light receiver 663.

The microphone 661 receives a voice uttered by a user. The microphone 661 may convert the received voice into an electrical signal and output the electrical signal to the processor 680. The user's voice may include, for example, a voice corresponding to a menu or function of the display device 600. For example, a recognition range of the microphone 661 is recommended to be 4 meters or less from the microphone 661 to the user's location, and the recognition range of the microphone 661 may vary depending on amplitude of the user's voice and surrounding conditions (e.g., speaker sound, surrounding noise).

The microphone 661 may be implemented integrally with or separately from the display device 600. A separate microphone 661 may be electrically connected to the display device 600 through the communication module 650 or the input/output module 670.

Microphone 661 may be omitted depending on the performance and structure of the display device 600.

The camera module 662 receives an image, e.g., successive frames, corresponding to a motion of the user including a gesture within a camera recognition range. For example, the recognition range of the camera module 662 may be a range of 0.1 to 5 m from the camera module 662 to the user. The motion of the user may include e.g., a motion of a portion of the user's body or a portion of the user such as the user's face, facial expression, hand, fist, or finger(s). The camera module 662 may convert a received image into an electrical signal and output the electrical signal to the processor 680 under the control of the processor 680.

The processor 680 may select a menu displayed on the display device 600 based on a received motion recognition result or perform control corresponding to the motion recognition result. For example, channel tuning, volume control, or pointer movement may be included.

The camera module 662 may include a lens (not shown) and an image sensor (not shown). The camera module 662 may use a plurality of lenses and image processing to support optical zooming or digital zooming. The recognition range of the camera module 662 may be set in various ways depending on the camera angle and the surrounding environmental condition. When the camera module 662 includes a plurality of cameras, the plurality of cameras may be used to receive a three dimensional (3D) still image or 3D motion.

The camera module 662 may be implemented integrally with or separately from the display device 600. An extra device (not shown) including a camera module 662 separate from display device 600 may be electrically connected to the display device 600 through the communication module 650 or the input/output module 670.

The camera module 662 may be omitted depending on the performance and structure of the display device 600.

The light receiver 663 receives an optical signal (including a control signal) received from an external control device (not shown) through a light window (not shown) of a bezel of the display 615. The light receiver 663 may receive an optical signal corresponding to a user input, e.g., touch, push, touching gesture, voice, or motion of the user, from a control device (not shown). A control signal may be extracted from the received optical signal under the control of the processor 680.

For example, the light receiver 663 may receive a signal corresponding to a pointing position of a control device (not shown) and forward the signal to the processor 680. For example, when a user interface screen for receiving data or a command from the user through the display 615 is displayed and the user wants to input data or a command to the display device 600 through the control device, the light receiver 663 may receive a signal corresponding to a motion of the control device when the user moves the control device while touching his/her finger on a touch pad (not shown) arranged on the control device, and may forward the signal to the processor 680. The light receiver 663 may receive a signal indicating that a certain button arranged on the control device has been pressed, and forward the signal to the processor 680. For example, when the user presses a touch pad (not shown) provided in a button type on the control device with his/her finger, the light receiver 663 may receive a signal indicating that the button-type touch pad (not shown) has been pressed, and forward the signal to the processor 680. For example, the signal indicating that the button-type touch pad (not shown) has been pressed may be used as a signal to select one of items.

The Input/output module 670 receives a video (e.g., a moving image), an audio (e.g., a voice, music, etc.), additional information (e.g., an EPG), or the like from outside of the display device 600 under the control of the processor 680. The input/output module 670 may include one of an HDMI port 671, a component jack 672, a PC port 673, and a USB port 674. The input/output module 670 may include a combination of the HDMI port 671, the component jack 672, the PC port 673, and the USB port 674.

The configuration and operation of the input/output module 670 may be implemented variously in embodiments of the disclosure.

The processor 680 controls general operation of the display device 600 and signal flows between the internal components of the display device 600, and performs a function of processing data. The processor 680 may run an operating system (OS) and various applications stored in the memory 690 at the user's request or when a predetermined condition is met.

The processor 680 may include a RAM (not shown) for storing a signal or data input from outside of the display device 600 and/or for use as a storage area corresponding to various tasks performed on the display device 600, a ROM (not shown) storing a control program to control the display device 600, and a processor (not shown).

The processor may include a graphic processing unit (not shown) for graphic processing corresponding to a video. The processor may be implemented as a system on chip (SoC) in which a core (not shown) and the GPU are integrated. The processor may include a single core, dual cores, triple cores, quad cores, and other multiple cores.

The processor may include a plurality of processors. For example, the processor may be implemented with a main processor (not shown) and a sub processor (not shown) activated in a sleep mode.

The GPU may use a calculator (not shown) and a renderer (not shown) to create a screen including various objects such as icons, images, text, etc. The calculator may use a user interaction detected by the detector (not shown) to calculate an attribute value such as a coordinate value, a shape, a size, color, etc., in which each of the objects may be displayed, based on the layout of the screen. The renderer creates screens in various layouts, which include an object, based on the attribute value calculated by the calculator. The screen created by the renderer is displayed in a display area of the display 615.

Figure 7:
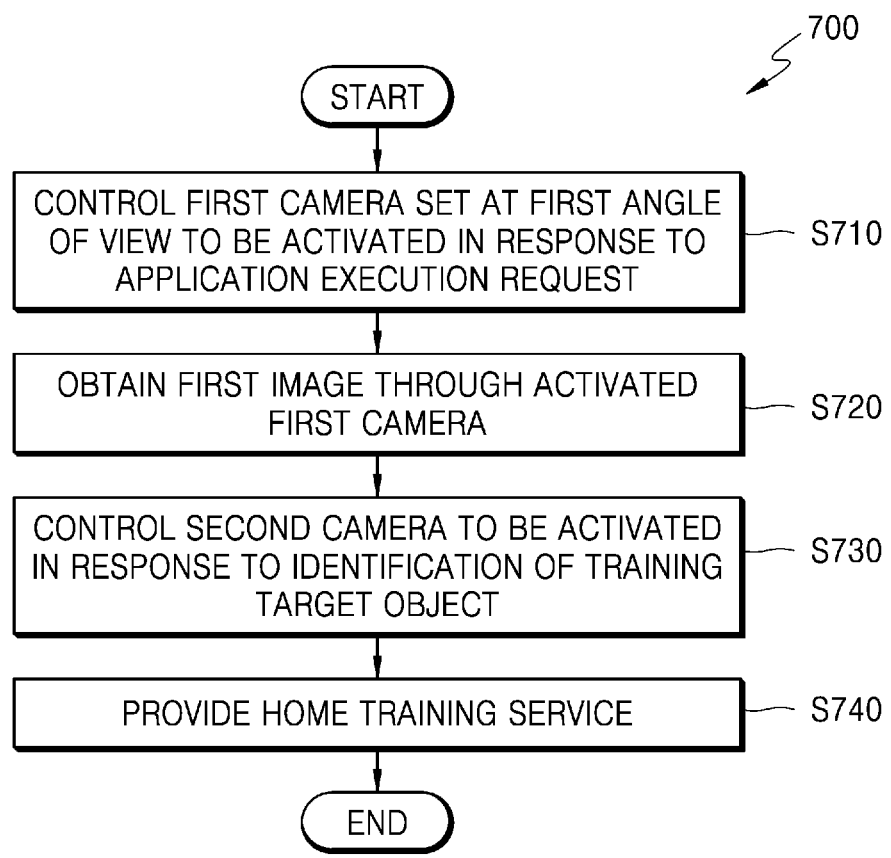
FIG. 7 is a flowchart illustrating an example method of operating an example display device, according to various embodiments.

FIG. 7 is a flowchart illustrating an example method of operating an example display device, according to various embodiments. Specifically, a method 700 of operating a display device shown in FIG. 7 may be performed by the display device 100, 200, 300, 400, 500 or 600 according to various embodiments of the disclosure as described above in connection with FIGS. 1 to 6. In describing the operations included in the method 700 of operating the display device, overlapping operations with those performed by the display device 100, 200, 300, 400, 500 or 600 described with reference to FIGS. 1 to 6 will not be repeated.

Furthermore, operations according to example embodiments of the disclosure as will be described in FIGS. 7 to 18 may be performed by the display device 100, 200, 300, 400, 500 or 600 according to the embodiments of the disclosure. For convenience of explanation, an occasion when the method 700 of operating the display device and operations as will be described in connection with FIGS. 8 to 18 are performed by the display device 500 as described in FIG. 5 will now be described by way of example.

Referring to FIG. 7, the method 700 of operating the display device is a method of operating the display device providing a home training service.

Specifically, in the method 700 of operating the display device, a first camera set at a first angle of view is controlled to be activated in response to a request to run an application for providing the home training service, in operation S710. Operation S710 may be performed under the control of the processor 240. The camera 230 may be included in the display device 500 or equipped in the form of being included in an external device (e.g., 401 of FIG. 4) connected through the communication interface 205.

For example, when the camera 230 includes a single camera, the first camera, the first angle of view may be set to have a maximum value in a viewing angle range of the first camera. In this case, the processor 240 may make the adjustment using an optical zooming or digital zooming function for the first camera to have the maximum angle of view. Narrowing the angle of view to narrow the field of view (FOV) is called zoom-in, and widening the angle of view to widen the FOV is called zoom-out. The processor 240 may control the first camera to be zoomed out to the maximum.

When the camera 230 includes a plurality of cameras having different angles of view, the processor 240 may identify the first camera having a maximum angle of view among the plurality of cameras. In other words, the first angle of view may be set to have a value corresponding to a maximum value of the viewing angle range that may be set for the plurality of cameras.

Operation S710 will be described in more detail in connection with FIG. 8.

Figure 8:
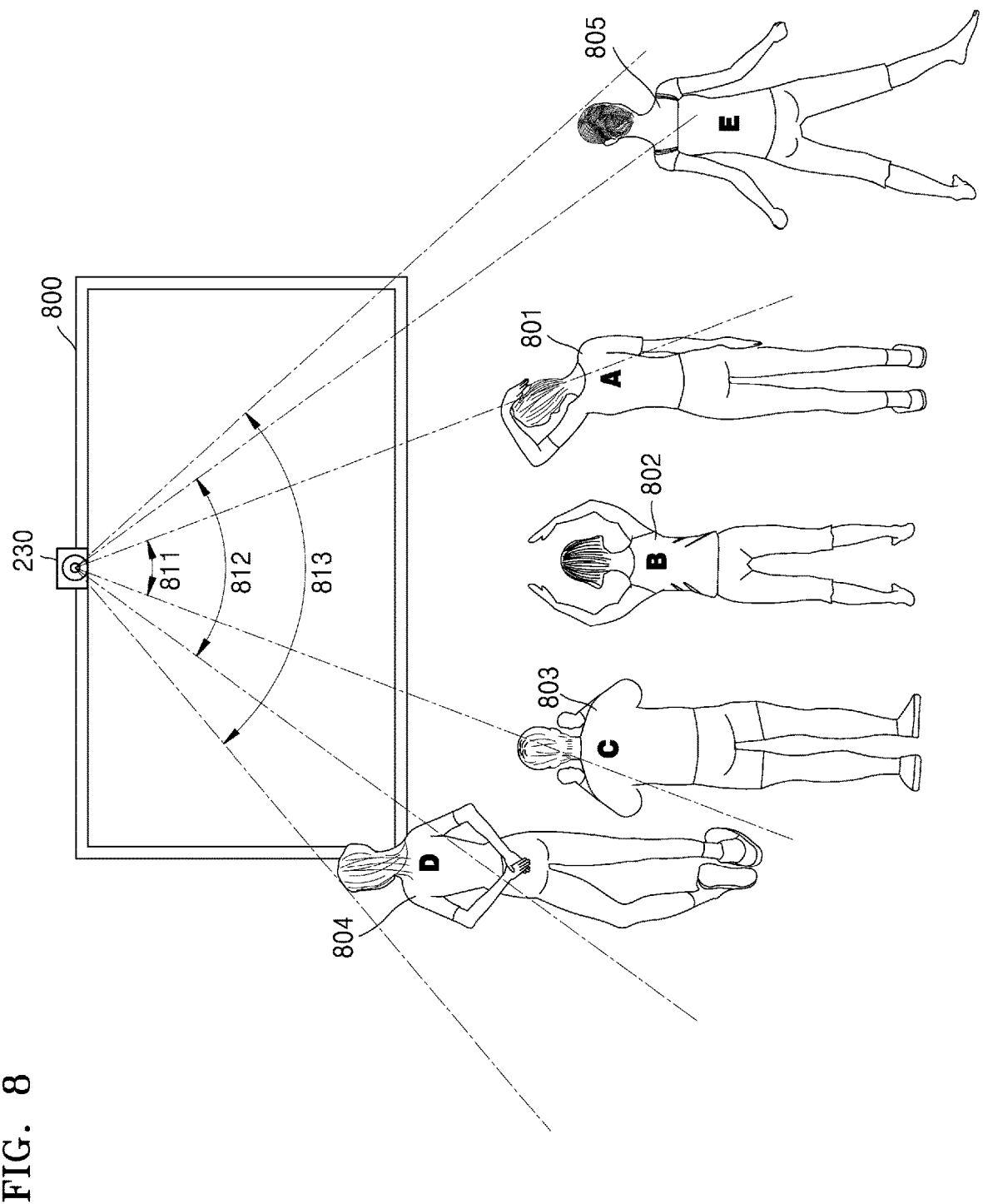
FIG. 8 is a diagram for describing an example camera used to provide an example home training service.

FIG. 8 is a diagram for describing an example camera used to provide an example home training service. In FIG. 8, the same components as in FIG. 5 are denoted by the same reference numerals, and a display device 800 may correspond to the display device 100, 200, 300, 400, 500 or 600 shown in FIGS. 1 to 6.

An occasion when the camera 230 available to the display device 800 includes a single camera is shown and described in FIG. 8 as an example. Referring to FIG. 8, the camera 230 may be manufactured and designed to have various angles of view. The camera 230 may be manufactured to have a fixed angle of view or a varying angle of view within a certain range. When the camera has an optically- or digitally-varying angle of view within a certain range, the camera may be called an optical zoom camera or a digital zoom camera.

Depending on the angle of view of the camera 230, the range shown in an image obtained by the camera 230 may vary. As shown, there may be 5 users 801, 802, 803, 804 and 805 in front of the display device 800. For example, angles of view 811, 812 and 813 may have values of 23 degrees, 47 degrees and 75 degrees, respectively. For convenience of explanation and naming, the angles of view 811, 812 and 813 may be referred to, for example, as 23-degree angle of view 811, 47-degree angle of view 812 and 75-degree angle of view 813, respectively.

When the angle of view of the camera 230 is the 23-degree angle of view 811, it may photograph only user B 802. When the angle of view of the camera 230 is the 47-degree angle of view 812, it may photograph user A 801, user B 802 and user C 803. When the angle of view of the camera 230 is the 75-degree angle of view 813, it may photograph user A 801, user B 802, user C 803, user D 804 and user E 805.

Alternatively, the camera 230 may include at least one of a plurality of cameras having different angles of view (e.g., a standard camera (e.g., a camera having an angle of view ranging from 40 to 60 degrees), a telecamera (e.g., a camera having an angle of view of 40 or less degrees), a wide-angle camera (e.g., a camera having an angle of view ranging from 60 to 80 degrees), an optically zoomable camera (e.g., a camera having an angle of view that is adjustable within a range of 60 to 80 degrees by physically adjusting the lens of the camera), and a digitally zoomable camera (e.g., a camera able to digitally adjust the capturing range)). In the example shown in FIG. 8, the camera 230 may use the telecamera to capture an image in the 23-degree angle of view 811, use the standard camera to capture an image in the 47-degree angle of view, and use a wide-angle camera to capture an image in the 75-degree angle of view.

Alternatively, the camera 230 may include an optically zoomable camera or a digitally zoomable camera. For example, a maximum angle of view of the camera 230 may be 80 degrees and a minimum angle of view may be 20 degrees. In the example of FIG. 8, the camera 230 may perform an optical-zoom or digital-zoom operation to adjust the angle of view to one of the 23-degree angle of view 811, the 47-degree angle of view 812 and the 75-degree angle of view.

When at least one user wants to use a home training service to capture an image of the user and provide coaching information for the user, a target object who is going to do home training needs to be accurately identified. The identified home training target object may then be photographed to provide the coaching information.

When the camera 230 is to be activated to obtain an image to identify the home training target object, it is common to activate a standard camera. An angle of view corresponding to 1:1 zoom (e.g., the 47-degree angle of view 812) may be included in a range of viewing angles of the standard camera, and when the standard camera is used, an image including only users A, B and C 801, 802 and 803 may be obtained. In this case, when the home training target object is to be identified based on the image obtained by the standard camera, user D 804 and user E 805 will not be considered as the home training target object. When user D 804 and user E 805 want to do home training, the user may operate the display device 800 by changing the angle of view of the camera 230 or switching the camera type to capture an image so that an image including user D 804 and user E 805 is obtained.

In other words, when there are many users present in a space where the display device 800 is located, and execution of a home training application is requested, all of the users may want to do home training or only some of them may want to do home training. Hence, all the at least one user present in the space where the display device 800 is located need to be identified, and among them (i.e., the users), a training target object needs to be identified and selected.

In an example embodiment of the disclosure, when a request to execute a home training application is received, the angle of view of the camera 230 may be switched to a maximum angle of view (e.g., the 75-degree angle of view 813) in response to the request, without an extra user input from the user. Accordingly, the camera 230 may photograph as wide space as possible, and photograph all users present in the space where the display device 800 is located. Hence, to select the home training target object, the at least one user who may use the display device 800 may all be considered. This may enable an image for identifying the home training object to be obtained conveniently and quickly without extra camera manipulation or image recapturing to obtain the image.

An example in which a maximum angle of view of at least one camera included in the camera 230 is the 75-degree angle of view 813 will now be described.

Turning back to FIG. 7, the first angle of view of operation S710 may be set to a value of more than 70 degrees (e.g., 75 degrees). In operation S710, the first camera may be a camera having an angle of view of 75 degrees 813. In other words, in operation S710, the processor 240 may control the camera 230 having a maximum angle of view, the 75-degree angle of view 813, to be activated.

In the method 700 of operating the display device, the first image may be obtained through the activated first camera, in operation S720. Operation S720 may be performed by the camera 230 under the control of the processor 240. Referring to FIG. 8, as the first image obtained by the first camera is an image corresponding to the 75-degree angle of view 813, it may be an image including all the 5 users 801, 802, 803, 804 and 805 in front of the display device 800.

Subsequently, a second camera set at a second angle of view different from the first angle of view is controlled to be activated in response to at least one of the at least one object included in the first image being identified as a training target object, in operation S730. Operation S730 may be performed by the processor 240.

For example, operation S730 may include identifying at least one of the at least one object included in the first image obtained in operation S720 as a training target object, and controlling the second camera set at a second angle of view different from the first angle of view to be activated, in response to the identifying of the training target object.

Specifically, in operation S730, the training target object may be identified based on the first image. Specifically, the training target object is at least one of the at least one object included in the first image. More specifically, the first image may be analyzed to detect human(s) included in the first image. The operation of detecting the human in the first image may be performed by using a computer vision technology, artificial intelligence (AI) object recognition, a machine learning technology, and the like.

Furthermore, detecting an object (e.g., a human) targeted in the first image may be performed by the processor 240, or by an external device receiving the first image (e.g., a server for performing AI operations). When the object detection operation is performed by an external device, the processor 240 of the display device 500 may control the communication interface 205 to transmit the first image to the external device. The external device (not shown) may then analyze the first image to detect an object (e.g., a human) targeted for detection, and transmit information about a result of the detecting to the communication interface 205 of the display device 500.

In another example, when the camera 230 is provided in a form of a separate device (e.g., an external camera) from the display device 500, the first image obtained by the camera 230 may be transmitted directly to an external device (e.g., a server for performing an AI operation) from the camera 230. The external device (not shown) may then analyze the first image to detect an object (e.g., a human) targeted for detection, and transmit information about a result of the detecting to the communication interface 205 of the display device 500. Accordingly, the processor 240 of the display device 500 may obtain information about a training target object (e.g., a user who is going to use the training service).

The processor 240 may identify the training target object of the at least one object included in the first image, in operation S730. The training target object may refer, for example, to a user who is going to exercise by following exercise poses included in a content while viewing the content. Alternatively, the training target object may refer to, for example, a user to receive a recommendation of a home training service and be led to doing exercise based on home training.

The operation of identifying the training target object in operation S730 will now be described in detail with reference to FIGS. 9 and 10.

Figure 9:
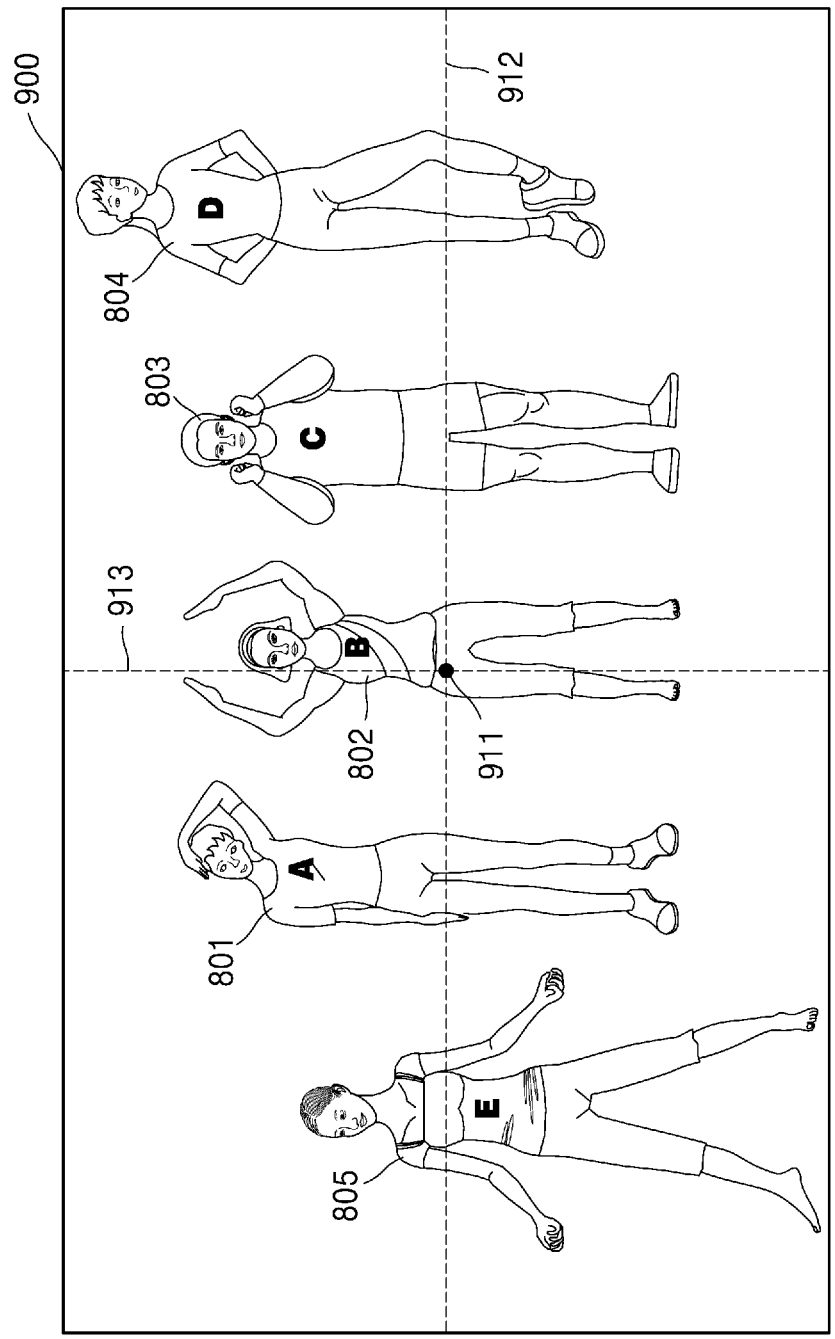
FIG. 9 is a diagram illustrating at least one object included in an image obtained by an example camera.

FIG. 9 is a diagram illustrating at least one object included in an image obtained by a camera. In FIG. 9, the same components as in FIG. 8 are shown with the same reference numerals.

Referring to FIG. 9, shown is a first image 900 obtained in operation S720. For example, the first image 900 may be an image obtained by the camera 230 set at the first angle of view, the 75-degree angle of view 813, as described in FIG. 7.

The processor 240 may identify a training target object based on the first image. Specifically, the processor 240 may set a target for detection in the first image to a human (or user) and detect a human in the first image. The processor 240 may recognize or extract a training target object, a user who is going to use the home training service among the detected at least one human. The operation of detecting the human in the first image and the operation of recognizing or extracting the training target object may be performed by using a computer vision technology, AI object recognition, a machine learning technology, and the like. Furthermore, the operation of detecting the human (or the user) in the first image and the operation of recognizing or extracting the training target object may be performed by an external device receiving the first image (e.g., a server for performing AI operations). A case in which the operation of detecting the human and the operation of recognizing or extracting the training target object are performed by the processor 240 will now be described for example.

For example, the processor 240 may calculate a score that represents a degree to which each of the at least one user detected in the first image intends to use home training. The score representing the degree to which home training is intended to be used may be referred to, for example, as an estimated score of intention of involvement. The processor 240 may identify at least one of the at least one user detected in the first image as the training target object based on the estimated score of intention of involvement. The processor 240 may select the training target object according to priority of the estimated score of intention of involvement for each of the at least one user. The processor 240 may display a list of training target objects through the display 220 according to priority of the estimated score of intention of involvement for each of the at least one user.

Specifically, the processor 240 may identify at least one of the at least one object as the training target object based on at least one of a location of the at least one object (specifically, a user) detected in the first image, a gaze direction of the at least one object, or a distance between the at least one object and the display device 400. Specifically, the estimated score of intention of involvement may be calculated based on at least one of a location of at least one object detected in the first image, a gaze direction of the at least one object, or a distance between the at least one object and the display device 400.

When the user is going to do home training, the user may be located not too far away from the display device 400 and may gaze at the screen of the display device 400. Furthermore, it is more likely that the user is located in a center region in front of the display device 400 to avoid or reduce discomfort in viewing the content for home training. Hence, the estimated score of intention of involvement may be calculated to be higher when the detected user is located closer to the display device 400, when the gaze of the detected user is directed to the screen of the display device 400, or when the detected user is located closer to the center region directly in front of the display device 400.

Referring to FIG. 9, based on the distance away from a center point 911 of the first image 900, the location of the detected user may be determined.

The following equation 1 is an example of a calculation to calculate the estimated score of intention of involvement.

$$S_{intent}(a) = S_{center}(a) * W_{center}(a) S_{distance}(a) * W_{distance}(a) + S_{focus}(a) * W_{focus}(a)$$ [Equation 1]

where Sintent(a) indicates the estimated score of intention of involvement. Scenter(a) may indicate a value of a score converted from a distance between the center point 911 of the first image 900 and a reference point in a human (e.g., a center point of a face). For example, Scenter(a) may have a value equal to or greater than 0 and equal to or smaller than 1.

Sdistance(a) is a value indicating a distance between the detected user and the display device 400, which may be a value equal to or greater than 0 and equal to or smaller than 1. For example, Sdistance(a) may be a value of a score converted from a facial size of the user in the first image (e.g., a ratio occupied by the facial height value in the image).

Sfocus(a) is a value of a score converted from a degree to which the detected user gazes at the screen of the display device 400, which may be a value equal to or greater than 0 and equal to or smaller than 1. Specifically, Sfocus(a) may be calculated using various methods of detecting a gaze of a human. For example, Sfocus(a) may be calculated based on a head pose estimation technology, a gaze direction detection technology, or a measurement method based on a degree to which the gaze direction is directed to a particular point on the display device 400.

Wcenter(a), Wdistance(a), and Wfocus(a) may be weight values applied to Scenter(a), Sdistance(a), and Sfocus(a), respectively. Wcenter(a), Wdistance(a), and Wfocus(a) may each be set to a value equal to or greater than 0 and equal to or smaller than 1. For example, Wcenter(a), Wdistance(a), and Wfocus(a) may be differently set based on a condition in which the display device 400 is located, features of the detected user, etc.

Apart from the equation 1, the intention of the user to do training may be determined using various methods to select a training target object.

The processor 240 may identify a user having the estimated score of intention of involvement equal to or higher than a limit value as the training target object. The processor 240 may select at least one user as the training target object in ascending order of the estimated score of intention of involvement. In another example, the processor 240 may control a user interface screen including a list of users detected in ascending order of the estimated score of intention of involvement to be displayed, and select a user chosen in the displayed user interface screen as the training target object.

Referring to FIG. 9, as user A 801, user B 802 and user C 803 each gaze at the front of the display device 400 and are located in a center region in front of the display device 400, estimated scores of intention of involvement of these users may be calculated to have values equal to or higher than the limit value. Accordingly, the processor 240 may identify user A 801, user B 802 and user C 803 of 5 users 801, 802, 803, 804 and 805 detected in the first image 901 as the training target object.

Figure 10:
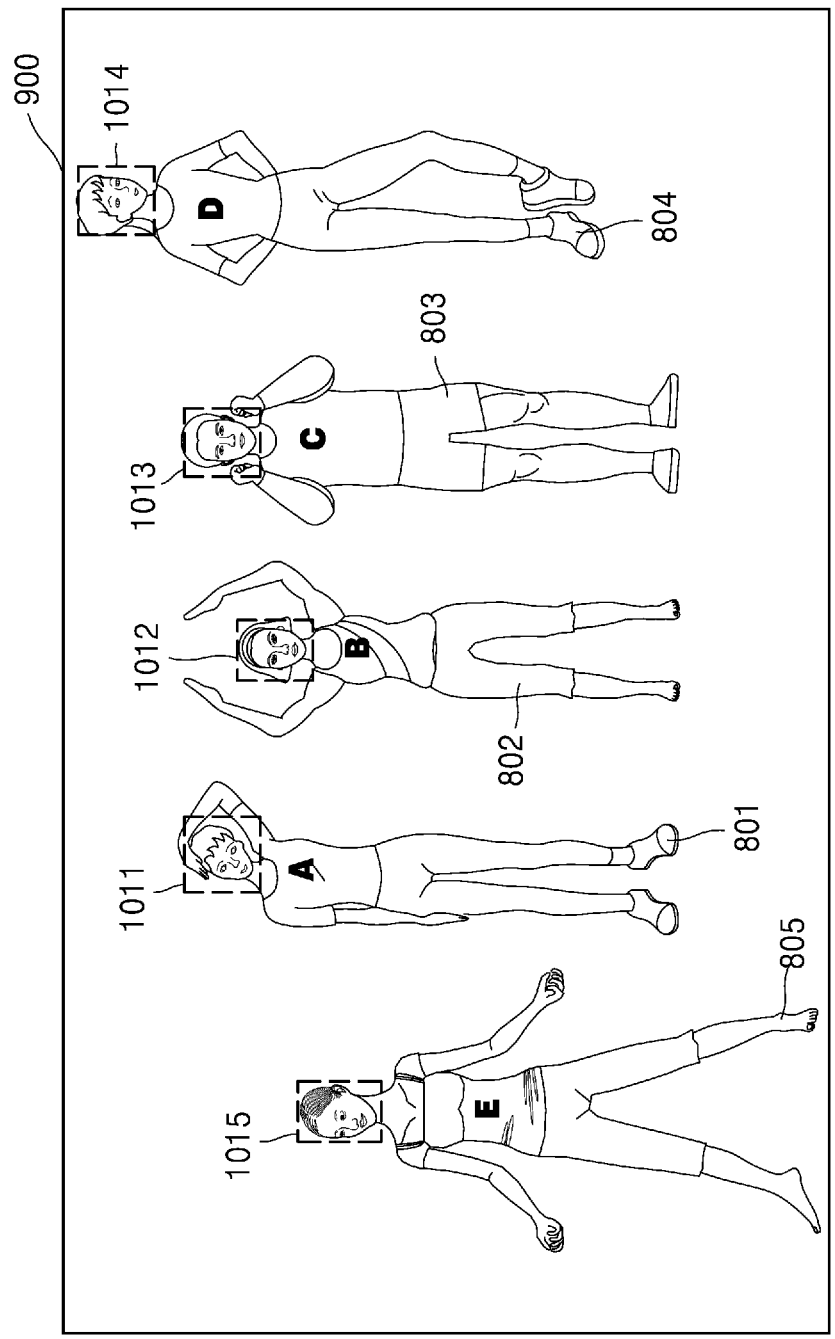
FIG. 10 is a diagram illustrating at least one object included in an obtained image.

FIG. 10 is a diagram illustrating at least one object included in an obtained image. In FIG. 10, the same components as in FIGS. 8 and 9 are shown with the same reference numerals.

In another example, the processor 240 may identify the training target object of the at least one object included in the first image based on a user input, in operation S730. Specifically, the processor 240 may control the user interface screen including the first image to be displayed on the display 220. The user may then input a user input to select at least one of the at least one object included in the first image to the display device 500 through the user interface 270 or the communication module 260.

The processor 240 may control a user interface screen representing selection cursors 1015, 1011, 1012, 1013 and 1014 for selecting five (5) users 801, 802, 803, 804 and 805 detected in the first image 900 to be displayed. The user may then input a user input to select or release selection of the selection cursors 1015, 1011, 1012, 1013 and 1014 to the display device 500 through the user interface 270 or the communication module 260. The display device 400 may select the training target object based on the received user input. For example, when the user inputs for selecting that select the selection cursor 1011, the selection cursor 1012 and the selection cursor 1013 to the display device 500, the processor 240 may select user A 801, user B 802 and user C 803 as the training target object.

In another example, when the user inputs user inputs that select the selection cursor 1011 and the selection cursor 1013 to the display device 500, the processor 240 may select user A 801 and user C 803 as the training target object.

Turning back to FIG. 7, in the method 700 of operating the display device, the home training service is provided for the training target object identified in operation S730, in operation S740. Specifically, in the method 700 of operating the display device, based on at least one image obtained through the second camera set at the second angle of view, the home training service is provided for the training target object in operation S730, in operation S740.

Operation S740 may be performed under the control of the processor 240.

Specifically, the processor 240 may control a content for training to be reproduced, and control coaching information for the training target object to be provided by photographing the training target object identified during the reproducing of the content. Specifically, the processor 240 may control the content for training to be reproduced through the display 220, control the camera 230 to photograph the identified training target object during the reproducing of the content, and obtain coaching information corresponding to the training target object based on the captured image. Subsequently, the processor 240 may control the display 220 or audio (not shown) to provide the obtained coaching information to be visually or audibly output to the user.

Figure 11:
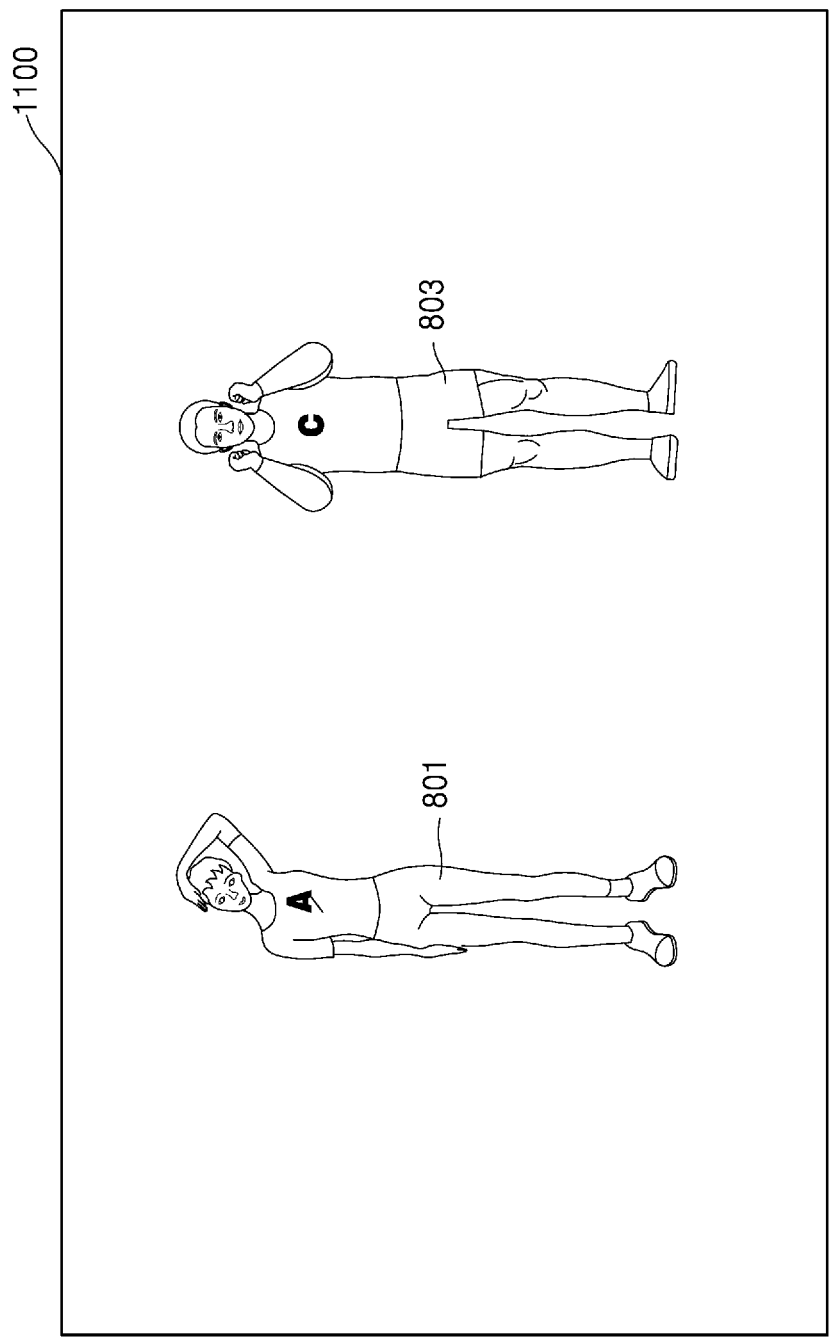
FIG. 11 is a diagram illustrating an example home training target object.

FIG. 11 is a diagram illustrating an example home training target object. In FIG. 11, the same components as in FIG. 8 are shown with the same reference numerals.

Referring to FIG. 11, an occasion when user A 801 and user C 803 are identified as the training target object is shown as an example. An image 1100 is an image that corresponds to the first image (e.g., 900) but includes only the training target object.

In an embodiment of the disclosure, the processor 240 may select a camera having the second angle of view among at least one camera used for the home training service based on the location of the training target object identified in operation S730. Furthermore, coaching information for the training target object may be obtained based on an image obtained by the camera having the second angle of view. For convenience of explanation, the camera having the second angle of view is referred to, for example, as the second camera.

Specifically, the processor 240 may control the angle of view or the capturing range of the at least one camera included in the camera 230 to be changed to fit the number of users selected as the training target object. For example, when the training target object is one, the processor 240 may use a camera having a narrow angle of view to include only one user as an object to be photographed to capture the one user who is the training target object.

Referring to FIG. 11, the processor 240 may identify user A 801 and user C 803 as the training target object in the first image 1100, and adjust the angle of view of the camera 230 to the second angle of view based on the locations of the identified user A 801 and user C 803. For example, the second angle of view may have a value smaller than the first angle of view. For example, the second angle of view may be an angle of view having a smaller value than the first angle of view. For example, when the first angle of view is an angle of view of a wide-angle camera, the second angle of view may be an angle of view of a standard camera (or normal camera) or telecamera. In another example, the second angle of view may be an angle of view which includes the training target object (e.g., user A 801 and user C 803) in the center of the screen. Alternatively, the second angle of view may be an angle of view which includes only the training target object (e.g., user A 801 and user C 803) among the at least one object included in the first image as an object to be photographed. Alternatively, the second angle of view may be an angle of view which includes the training target object (e.g., user A 801 and user C 803) in the center and the whole area of the captured image.

Figure 12:
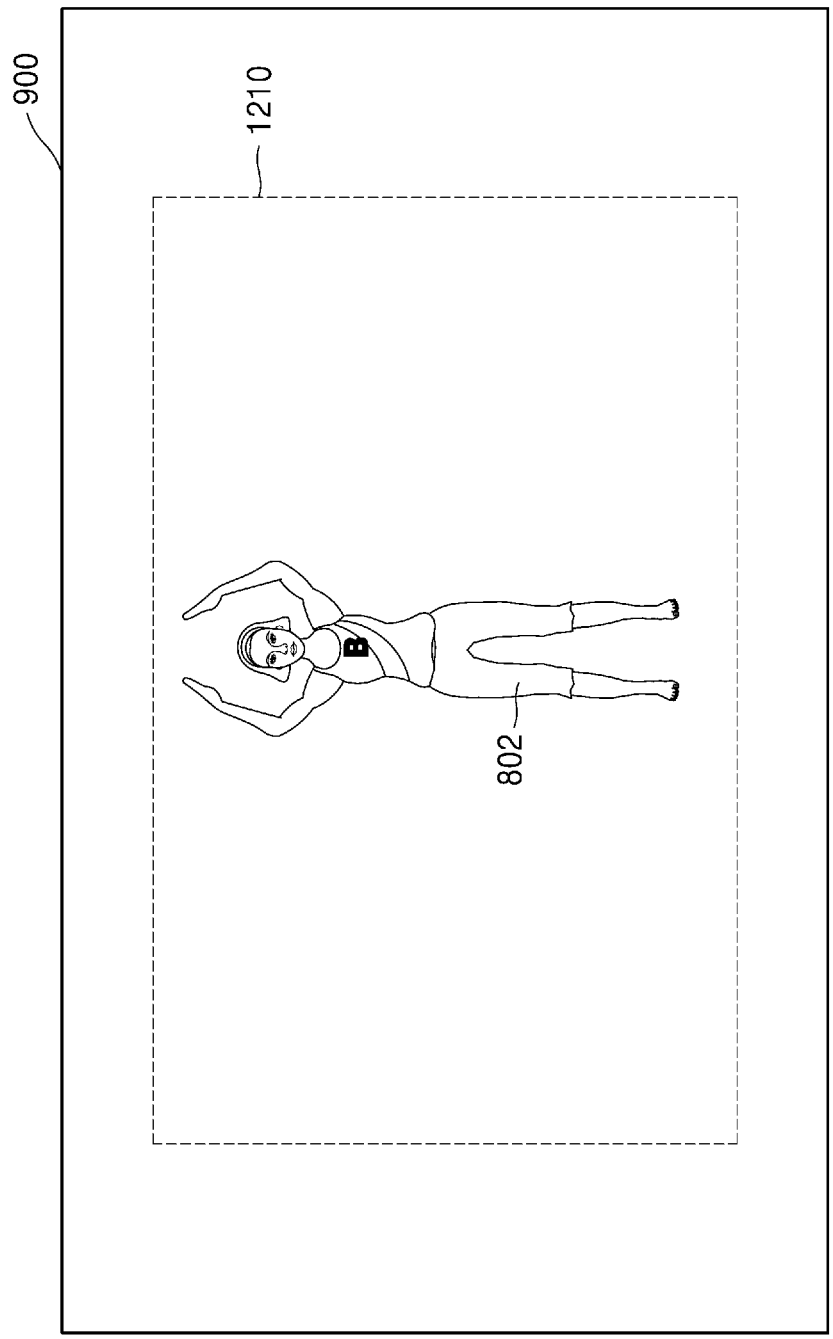
FIG. 12 is a diagram for describing an example camera for photographing an example home training target object.

FIG. 12 is a diagram for describing an example camera for photographing an example home training target. In FIG. 12, the same components as in FIGS. 8 and 9 are shown with the same reference numerals.

In an example embodiment of the disclosure, the processor 240 may select the second camera having the second angle of view among at least one camera used for the home training service based on at least one of the number and the location of the training target object identified in operation S730.

Turning back to FIGS. 8 and 9, after the first image 900 is obtained by using the first camera having the 75-degree angle of view 813, only user B 802 of the users detected in the first image 900 may be identified as the training target object in operation S730. In this case, the processor 240 may select the second camera having the second angle of view based on the location of user B 802 identified as the training target object. Specifically, the processor 240 may select the second camera having a narrow angle of view to photograph only one user because there is only one user B 802 identified as the training target object.

Referring to FIG. 12, the second angle of view may correspond to a capturing range 1210 in which to take a picture around user B 802. Hence, the processor 240 may photograph the training target object, user B 802, using the second camera having the second angle of view among the at least one camera included in the camera 230. Accordingly, the processor 240 may generate and provide the user with coaching information for user B 802 who is following home training by analyzing and processing an image obtained by the second camera.

Specifically, the processor 240 may select the second camera having the second angle of view among the at least one camera used for the home training service based on the number of the identified training target object. For example, when the number of users who are the training target object is 1, a camera set at a narrow angle of view may be used to photograph the training target object. In another example, when there are multiple users who are the training target object, a camera set at a wide angle of view to photograph all of the multiple users may be used to photograph the training target object.

There may be a case that the camera 230 includes only one camera, the first camera. The first camera may be a camera having an adjustable angle of view (e.g., an optically zoomable camera or a digitally zoomable camera). In this case, the processor 240 may change the angle of view of the first camera to the second angle of view based on at least one of the location and number of the identified training target object. Coaching information for the training target object may be obtained based on an image obtained by the first camera having the second angle of view while the home training service is being executed.

Depending on whether the capturing angle of the camera 230 is changeable or not changeable, the processor 240 may photograph the training target object with the second camera. An operation of the display device, e.g., 500, performed in the case that the capturing angle of the camera 230 is not changeable will be described in connection with FIG. 13, and an operation of the display device, e.g., 500, performed in the case that the capturing angle of the camera 230 is changeable will be described in connection with FIG. 14.

Figure 13:
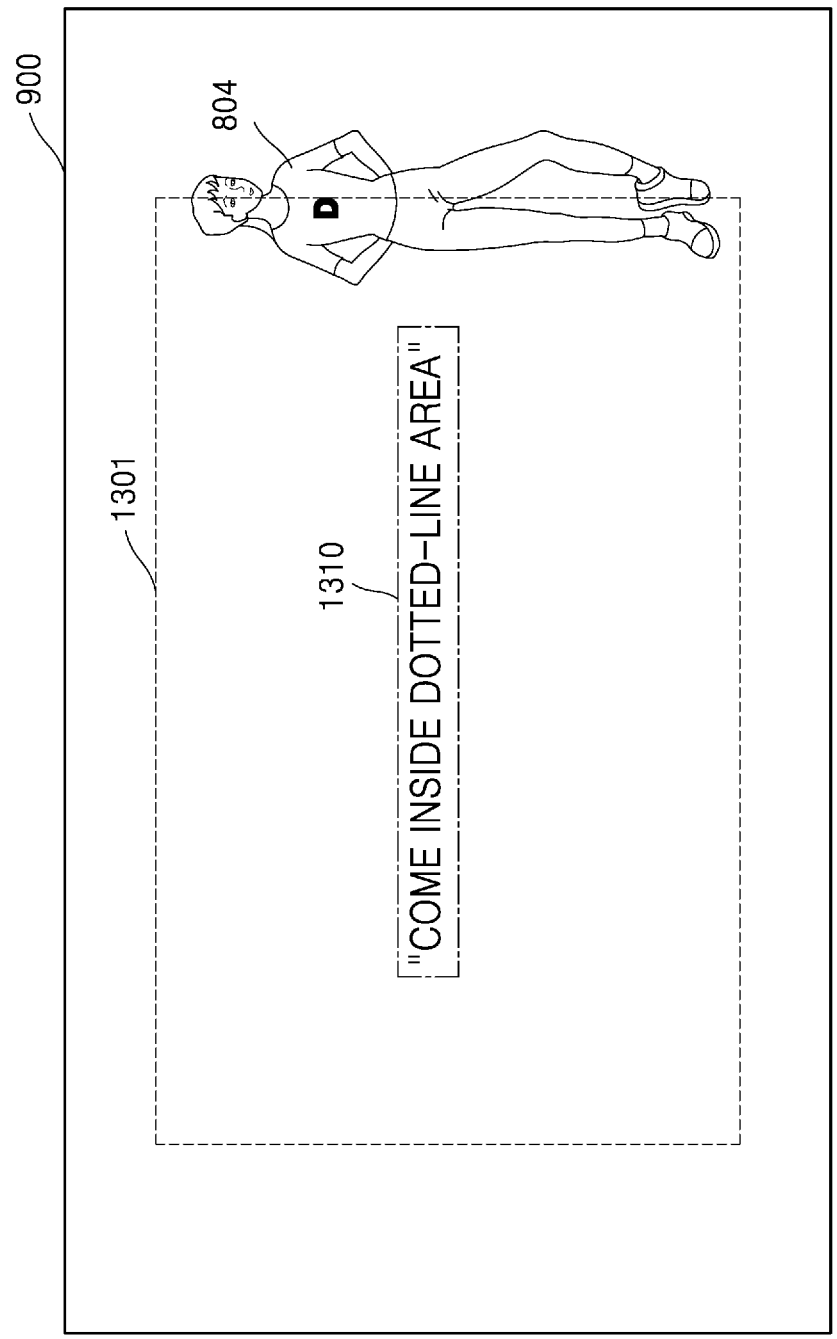
FIG. 13 is a diagram illustrating an example user interface screen output by an example display device, according to various embodiments.

FIG. 13 is a diagram illustrating an example user interface screen output by an example display device, according to various embodiments. In FIG. 13, the same components as in FIGS. 8 and 9 are shown with the same reference numerals.

In an example embodiment of the disclosure, there may be a case that the camera 230 has a changeable angle of view but unchangeable capturing angle. In this case, the processor 240 may control a message 1310 guiding capturing to be output on the first image 900 before photographing the training target object.

In FIG. 13, illustrated is an example in which only user D 804 is identified as the training target object. The processor 240 may adjust the angle of view to fit the training target object, user D 804. The angle of view adjusted to fit user D 804 may correspond to a capturing range 1301. To photograph user D 804 at the adjusted angle of view, the processor 240 may control a user interface screen on which the message 1310 is displayed on the first image 900 including an indication indicating the capturing range 1301 at the second angle of view adjusted for user D 804 to be displayed.

An image including the message 1310 and included in the user interface screen may be the whole or part of the first image 900. In FIG. 13, illustrated is an example in which the message 1310 is displayed on the whole of the first image 900.

Figure 14:
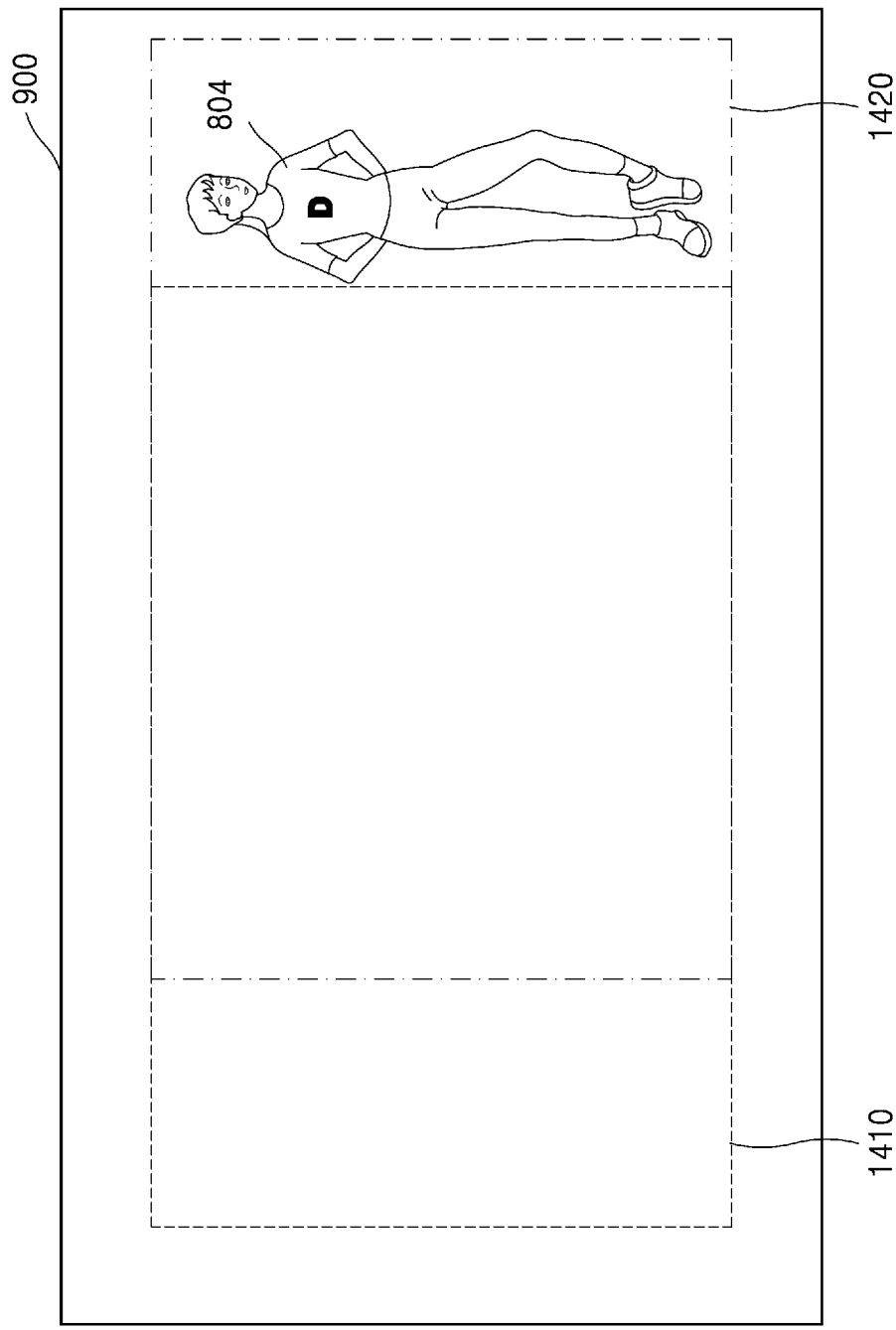
FIG. 14 is a diagram for describing an example camera for photographing an example home training target object.

FIG. 14 is another diagram for describing an example camera for photographing an example home training target. In FIG. 14, the same components as in FIGS. 8 and 9 are shown with the same reference numerals.

In an example embodiment of the disclosure, there may be a case that the camera 230 has a changeable angle of view and a changeable capturing angle. In this case, the processor 240 may change the capturing angle of the second camera having the second angle of view based on at least one of the location and number of the identified training target object, before photographing the training target object. The training target object may then be photographed by the second camera having the changed capturing angle.

FIG. 14 illustrates an example in which only user D 804 is identified as the training target object. The processor 240 may adjust the angle of view and the capturing angle to fit the training target object, user D 804. The angle of view adjusted to fit user D 804 may correspond to a capturing range 1410. The processor 240 may control the second camera to capture a capturing range 1420 by changing the capturing angle of the second camera having the adjusted angle of view.

Figure 15:
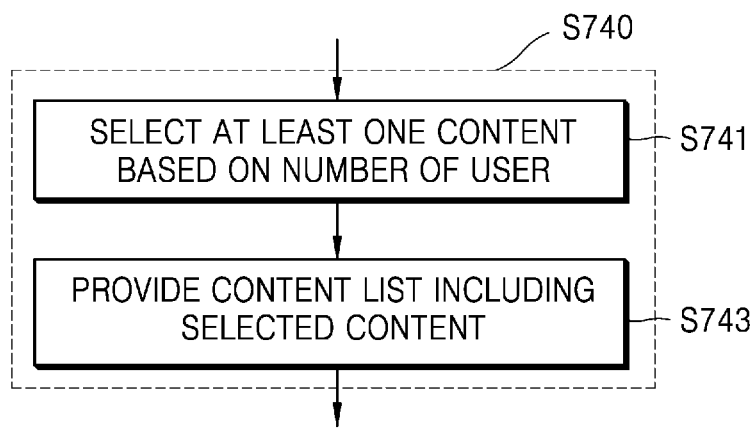
FIG. 15 is a flowchart for describing example operation S740 described in FIG. 7.

FIG. 15 is a flowchart for describing example operation S740 described in FIG. 7.

Referring to FIG. 15, in operation S740, based on the number of users corresponding to the training target object identified in operation S730, at least one of a plurality of contents may be selected in operation S741. The display 220 may be controlled to output a content list including the at least one content selected in operation S741, in operation S743.

For example, when the number of users, the identified training target object, is 1, the processor 240 may select at least one sport for one person and display a list of contents corresponding to the selected sport. In another example, when the number of users, the identified training target object, is 2, the processor 240 may select at least one sport for two persons and display a list of at least one content corresponding to the selected sport, in operation S743. The at least one content of the sport corresponding to the number of users may have high priority or may be in high ranks in the content list.

Figure 16:
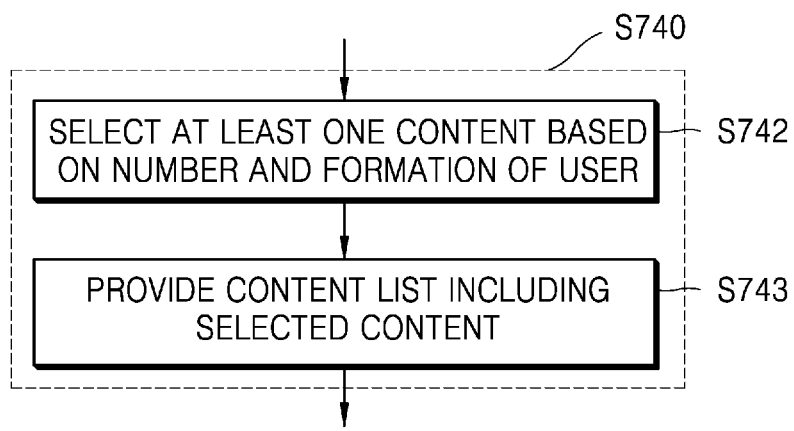
FIG. 16 is a flowchart for describing example operation S740 described in FIG. 7.

FIG. 16 is a flowchart for describing example operation S740 described in FIG. 7.

Referring to FIG. 16, in operation S740, based on the formation and the number of users corresponding to the training target object identified in operation S730, at least one of a plurality of contents may be selected in operation S742. The display 220 may be controlled to output a content list including the at least one content selected in operation S741, in operation S743. The formation may be identified based on a relative position between the users included in the training target object. For example, when there are 2 users included in the training target object, the formation may be identified based on a relative distance between the 2 users. For example, the relative distance may be set to a value equal to or greater than 0 and equal to or smaller than 1.

For example, when there are 2 users who are the identified training target object and the 2 users are located in a formation of being away from each other (for example, at a relative distance of 0.5 or more), the processor 240 may select at least one sport that may be played in a state of being away from each other among the sports for 2 persons, and display a list of contents corresponding to the selected sports.

In another example, when there are 2 users who are the identified training target object and the 2 users are located in a formation of being close to each other (for example, at a relative distance of less than 0.5 or at a relative distance of 0.2), the processor 240 may select at least one sport that may be played by 2 users in a state of being close to each other among the sports for 2 persons, and display a list of contents corresponding to the selected sports. The sport selected based on at least one of the formation and number of users will be described in detail in connection with FIGS. 17 and 18.

The content that may be reproduced in the home training service may include metadata that represents at least one of corresponding formation or sport. In this case, the processor 240 may identify the content corresponding to at least one of the number or formation of users who are the training target object identified among the plurality of available contents, based on the metadata included in the content.

FIG. 17 is a diagram for describing example content provided in an example home training service. In FIG. 17, the same components as in FIGS. 8 and 11 are shown with the same reference numerals.

Referring to FIG. 17, when user A 801 and user C 803 are identified as the training target object, the number of the users may be 2. The formation of the users may be represented with a relative distance between user A 801 and user C 803. For example, the relative distance may be a relative value that represents a distance between a center point 1701 of user A 801 and a center point 1702 of user C 803, and may have a value of 0.5 as an example in FIG. 17. Accordingly, the processor 240 may select a sport suitable for a case in which there are 2 users and the relative distance is 0.5. For example, a tug-of-war with both hands for 2 persons may be selected for the sport, and the processor 240 may control a content list including a content 1700 corresponding to the tug-of-war with both hands for 2 persons to be displayed.

FIG. 18 is a diagram for describing example content provided in an example home training service. In FIG. 18, the same components as in FIG. 8 are shown with the same reference numerals.

Referring to FIG. 18, when user B 802 and user C 803 are identified as the training target object, the number of the users may be 2. The formation of the users may be represented with a relative distance between user B 802 and user C 803. For example, the relative distance may be a relative value that represents a distance between a center point 1801 of user B 802 and a center point 1802 of user C 803, and may have a value of 0.2 as an example in FIG. 18. Accordingly, the processor 240 may select a sport that fits a case in which there are 2 users and the relative distance is 0.2. For example, a horizontal tug-of-war with one hand for 2 persons may be selected for the sport, and the processor 240 may control a content list including a content 1810 corresponding to the horizontal tug-of-war for 2 persons to be displayed.

In an example embodiment of the disclosure, based on at least one of the number or formation of users identified as the training target object, at least one of a plurality of available contents may be identified and provided for a user. Accordingly, a content list that is more suitable for the user's intention may be provided, increasing convenience and satisfaction of the user.

A method of operating a display device according to an example embodiment of the disclosure may be implemented in program instructions which are executable by various computing devices and recorded in computer-readable media. Furthermore, an embodiment of the disclosure may provide a computer-readable recording medium having one or more programs including instructions to perform a method of operating the display device recorded thereon.

The computer-readable media may include program commands, data files, data structures, etc., separately or in combination. The program commands recorded on the computer-readable media may be designed and configured specially for the disclosure, or may be well-known to those of ordinary skill in the art of computer software. Examples of the computer readable recording medium include ROMs, RAMs, Compact Disc (CD)-ROMs, magnetic tapes, floppy disks, optical data storage devices, etc. The computer readable recording medium can also be distributed over network-coupled computer systems so that the computer readable code is stored and executed in a distributed fashion. Examples of the program commands include not only a machine code made by a compiler but also include a high-level programming language to be executed in a computer by using an interpreter.

The machine-readable storage medium may be provided in the form of a non-transitory storage medium. The term 'non-transitory storage medium' may refer to a tangible device without including a signal, e.g., electromagnetic waves, and may not distinguish between storing data in the storage medium semi-permanently and temporarily. For example, the non-transitory storage medium may include a buffer that temporarily stores data.

In an example embodiment, the aforementioned method according to the various example embodiments of the disclosure may be provided in a computer program product. The computer program product may be a commercial product that may be traded between a seller and a buyer. The computer program product may be distributed in the form of a storage medium (e.g., a compact disc read only memory (CD-ROM)), through an application store (e.g., Play Store™), directly between two user devices (e.g., smart phones), or online (e.g., downloaded or uploaded). In the case of online distribution, at least part of the computer program product (e.g., a downloadable app) may be at least temporarily stored or arbitrarily created in a storage medium that may be readable to a device such as a server of the manufacturer, a server of the application store, or a relay server.

Specifically, a computer program product including a recording medium having a program stored thereon to perform a method of operating a display device may be implemented in an embodiment of the disclosure.

Several embodiments of the disclosure have been described, but it will be understood that various modifications can be made without departing the scope of the disclosure. Thus, it will be apparent to those ordinary skilled in the art that the disclosure is not limited to the embodiments described, but can encompass not only the appended claims but the equivalents.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. A display device comprising:
a display;
at least one processor including processing circuitry; and
memory storing at least one instruction,
wherein the at least one instruction, when executed, configures the at least one processor to individually or collectively control the display device to:
  activate a first camera set at a first angle of view in response to a request to execute an application for providing a home training service,
  obtain a first image through the activated first camera,
  detect at least one person included in the first image,
  for each respective person, obtain a score representing an intention of the respective person to use the home training service,
  identify at least one training target using the score for each respective person,
  obtain at least one second image including the at least one training target using a second angle of view different from the first angle of view, wherein the second angle of view is based on at least one of a number of the at least one training target in the first image or a location of the at least one training target in the first image, and
  provide the home training service based on the at least one second image.

2. The display device of claim 1, wherein the first angle of view is larger than the second angle of view.

3. The display device of claim 1, wherein the first camera is a wide-angle camera among at least one camera used for the home training service.

4. The display device of claim 1, further comprising a communication module, including a communication circuit, configured to communicate with at least one camera, wherein the at least one instruction, when executed, configure the at least one processor to individually or collectively control the display device to identify a camera having a maximum angle of view among the at least one camera as the first camera, and activate the first camera in response to the request to execute the application.

5. The display device of claim 1, further comprising at least one camera, wherein the at least one instruction, when executed, configure the at least one processor to individually or collectively control the display device to identify a camera having a maximum angle of view among the at least one camera as the first camera, and activate the first camera in response to the request to execute the application.

6. The display device of claim 1, wherein the at least one instruction, when executed, configure the at least one processor to individually or collectively control the display device to:
select the second camera having the second angle of view among at least one camera used for the home training service, wherein the at least one second image is obtained from the second camera, and
obtain coaching information for the at least one training target, based on the at least one second image.

7. The display device of claim 1, wherein the at least one instruction, when executed, configure the at least one processor to individually or collectively control the display device to:
change the first angle of view of the first camera to the second angle of view, wherein the at least one second image is obtained from the first camera having the changed angle of view, and
obtain coaching information for the at least one training target based on the at least one second image.

8. The display device of claim 1, wherein the score for each respective person is based on at least one of a location of the at least one person, a gaze direction of the at least one person, or a distance between the at least one person and the display device.

9. The display device of claim 1, wherein the at least one instruction, when executed, configure the at least one processor to individually or collectively control the display device to:
select at least one of a plurality of contents, based on a number of users corresponding to the identified training target object, and
control the display to display a content list including the selected at least one content.

10. The display device of claim 9, wherein the at least one instruction, when executed, configure the at least one processor to individually or collectively control the display device to select at least one of a plurality of contents, based on a number of users corresponding to the identified training target object, and a formation of the users.

11. The display device of claim 1, wherein the at least one instruction, when executed, configure the at least one processor to individually or collectively control the display device to obtain the at least one second image from a capturing angle different from a capturing angle for capturing the first image.

12. The display device of claim 1, wherein the at least one instruction, when executed, configure the at least one processor to individually or collectively control the display device to display on the display a list of persons detected in the first image ordered according to the score for each respective person.

13. The display device of claim 12, wherein the at least one instruction, when executed, configure the at least one processor to individually or collectively control the display device to identify the at least one training target based on input for selecting persons from the ordered list.

14. A method of operating a display device for providing a home training service, the method comprising:
activating a first camera set at a first angle of view in response to a request to execute an application for providing a home training service;
obtaining a first image through the activated first camera;
detecting at least one person included in the first image;
for each respective person, obtain a score representing an intention of the respective person to use the home training service;
identify at least one training target using the score for each respective person;
obtaining at least one second image including the at least one training target using a second angle of view different from the first angle of view in response to at least one of at least one object included in the first image being identified as a training target object, wherein the second angle of view is based on at least one of a number of the at least one training target in the first image or a location of the at least one training target in the first image; and
providing the home training service based on the at least one second image.

15. The method of claim 14, wherein the first angle of view is larger than the second angle of view.

16. The method of claim 14, wherein the first camera is a wide-angle camera among at least one camera used for the home training service.

17. The method of claim 14, further comprising:
obtaining coaching information for the at least one training target based on the at least one second image; and
providing the coaching information while the home training service is being provided.

18. The method of claim 14, further comprising:
selecting the second camera having the second angle of view among at least one camera used for the home training service, wherein the at least one second image is obtained from the second camera; and
activate the second camera.

19. At least one non-transitory computer-readable storage media storing instructions which, when executed by at least one processor, configure a display device to perform operations comprising:
activating a first camera set at a first angle of view in response to a request to execute an application for providing a home training service;
obtaining a first image through the activated first camera;
detecting at least one person included in the first image;
for each respective person, obtain a score representing an intention of the respective person to use the home training service;
identify at least one training target using the score for each respective person;
obtaining at least one second image including the at least one training target using a second angle of view different from the first angle of view in response to at least one of at least one object included in the first image being identified as a training target object, wherein the second angle of view is based on at least one of a number of the at least one training target in the first image or a location of the at least one training target in the first image; and providing the home training service based on the at least one second image.

\* \* \* \* \*